(12) United States Patent
Nakatani et al.

(10) Patent No.: US 7,790,441 B2
(45) Date of Patent: Sep. 7, 2010

(54) POLYMERASE CHAIN REACTION KIT AND METHOD OF MANUFACTURING THE SAME

(75) Inventors: Masaya Nakatani, Takarazuka (JP); Tetsuo Yukimasa, Nara (JP)

(73) Assignee: Panasonic Corporation, Osaka (JP)

( * ) Notice: Subject to any disclaimer, the term of this patent is extended or adjusted under 35 U.S.C. 154(b) by 130 days.

(21) Appl. No.: 12/149,147

(22) Filed: Apr. 28, 2008

(65) Prior Publication Data

US 2008/0308529 A1 Dec. 18, 2008

Related U.S. Application Data

(62) Division of application No. 10/485,342, filed as application No. PCT/JP03/08467 on Jul. 3, 2003, now Pat. No. 7,384,782.

(30) Foreign Application Priority Data

Jul. 5, 2002 (JP) .............................. 2002-197038

(51) Int. Cl.
*C12M 1/00* (2006.01)
(52) U.S. Cl. .................................................. 435/288.5
(58) Field of Classification Search ........................ None
See application file for complete search history.

(56) References Cited

U.S. PATENT DOCUMENTS

| 4,683,202 | A |   | 7/1987 | Mullis |   |
|---|---|---|---|---|---|
| 5,455,175 | A |   | 10/1995 | Wittwer et al. |   |
| 5,939,312 | A |   | 8/1999 | Baier et al. |   |
| 6,033,880 | A |   | 3/2000 | Haff et al. |   |
| 6,136,212 | A | * | 10/2000 | Mastrangelo et al. | ......... 216/49 |
| 6,143,496 | A |   | 11/2000 | Brown et al. |   |
| 6,168,948 | B1 |   | 1/2001 | Anderson et al. |   |
| 6,613,560 | B1 |   | 9/2003 | Tso et al. |   |
| 2001/0041357 | A1 |   | 11/2001 | Fouillet et al. |   |
| 2005/0118584 | A1 | * | 6/2005 | Nomura et al. | ................. 435/6 |

FOREIGN PATENT DOCUMENTS

| EP | 0733714 A2 | 9/1996 |
|---|---|---|
| JP | 62-281 | 1/1987 |
| JP | 2001-149059 A | 6/2001 |
| JP | 2002-207031 A | 7/2002 |
| JP | 2003-083965 A | 3/2003 |

* cited by examiner

*Primary Examiner*—Kenneth R. Horlick
*Assistant Examiner*—David C Thomas
(74) *Attorney, Agent, or Firm*—Steptoe & Johnson LLP

(57) ABSTRACT

The present invention provides a kit employed for polymerase chain reaction. The kit has a cavity and a flow channel on a substrate. The flow channel is separated from the cavity by at least a barrier formed along the cavity. Such a structure allows the cavity to be filled with a sample solution even in minute quantities. At the same time, the structure can provide a sample solution with a rapid temperature-control. The structure can therefore contribute to accelerated polymerase chain reaction.

12 Claims, 19 Drawing Sheets

POLYMERASE CHAIN REACTION KIT AND METHOD OF MANUFACTURING THE SAME

REFERENCE TO RELATED APPLICATIONS

This application is a divisional of application Ser. No. 10/485,342 filed Jan. 30, 2004, which is a national stage of PCT International Application No. PCT/JP03/08467 filed Jul. 3, 2003, which claims the benefit of Japanese Patent Application No. 2002-197038 filed Jul. 5, 2002.

TECHNICAL FIELD

The present invention relates to a kit or a reactor for amplifying nucleic acid through polymerase chain reaction and a manufacturing method thereof.

BACKGROUND ART

Recent years have seen technical advances on elucidating genetic information. In the medical field, analyzing disease-relating gene can provide a cure for a disease at a molecule level. Gene diagnosis enables patients to have medical treatment suitable for an individual case. Similarly, using genetic information, pharmacists identify a protein molecule of antibodies and hormones to produce medicines. Even in the agricultural field or food industries, many products benefit from the gene information.

In the techniques handling gene information, scientists put emphasis on the polymerase chain reaction method. With the polymerase chain reaction method, a certain portion of a gene can be amplified in large quantity. Not only for research and development in the molecular biology, the method is widely used in various fields, such as medical microbiology, a clinical diagnosis of hereditary diseases or forensic medicine. Particularly, in the field of the clinical gene diagnosis, it is desirable to be able to analyze the specimens as many as, and as quick as possible. That is, the process of the polymerase chain reaction should be accelerated with a smaller quantity of specimens.

A polymerase chain reaction method is disclosed in Japanese Patent Non-examined Publication No. S62-281. The polymerase chain reaction method is formed of the following three steps of: i) thermal denaturation, ii) annealing, and iii) extension reaction. The cycle of the three steps is repeatedly carried out 30 to 35 times. Firstly, in the thermal denaturation step, the double helix of DNA is separated into individual strands. Next, in the annealing step, a primer is bonded with the strand. Then, in the extension reaction step, polymerase catalyses the replication of DNA. These steps have each necessary condition. Especially, in the annealing step, the temperature depends on the Tm value of a primer to be used. They are usually carried out under 94° C. for 1 min. for the thermal denaturation step; 50 to 60° C. for 1 min. for the annealing step; and 72° C. for 1-5 min. for the extension reaction step.

To complete the polymerase chain reaction, as described above, a temperature-shift with a variation of approx. 40° C. has to be repeated over 30 times. According to a conventional equipment for the polymerase chain reaction, feeding a sample solution into a polypropylene tube (hereinafter referred to as a tube) and then controlling the temperature of the solution in the tube by using an aluminum block (hereinafter, a block). This requires over hours to complete the polymerase chain reaction, mainly because of taking time to shift the temperature of the sample solution to a proper temperature. It takes much time to shift the temperature of the block, and then to transmit the temperature of the block to the sample solution through the tube.

The sample-consuming tube is another problem—due to difficulty of making the tube small, a sample solution with an amount of 10 to 100 micro liters is needed per tube. Clinical treatment requires a gene diagnosis, awaiting an improved structure with which the polymerase chain reaction can be completed in a shorter time with less amount of the sample solution.

DISCLOSURE OF THE INVENTION

The polymerase chain reaction kit contains i) a substrate having a cavity and a flow channel for a heating medium, both separated by a barrier, and ii) a cover plate. The cover plate seals at least one of the cavity and the flow channel. The method of manufacturing the kit for the polymerase chain reaction includes the steps of a) forming a cavity and a flow channel, both separated by a barrier, on the surface of a substrate, b) attaching the substrate with a cover plate, c) connecting the cavity to a sample-solution inlet exposed to the outside, and d) connecting the flow channel to an inlet and an outlet exposed to the outside.

DETAILED DESCRIPTION OF PREFERRED EMBODIMENTS

First Exemplary Embodiment

Figure 1:
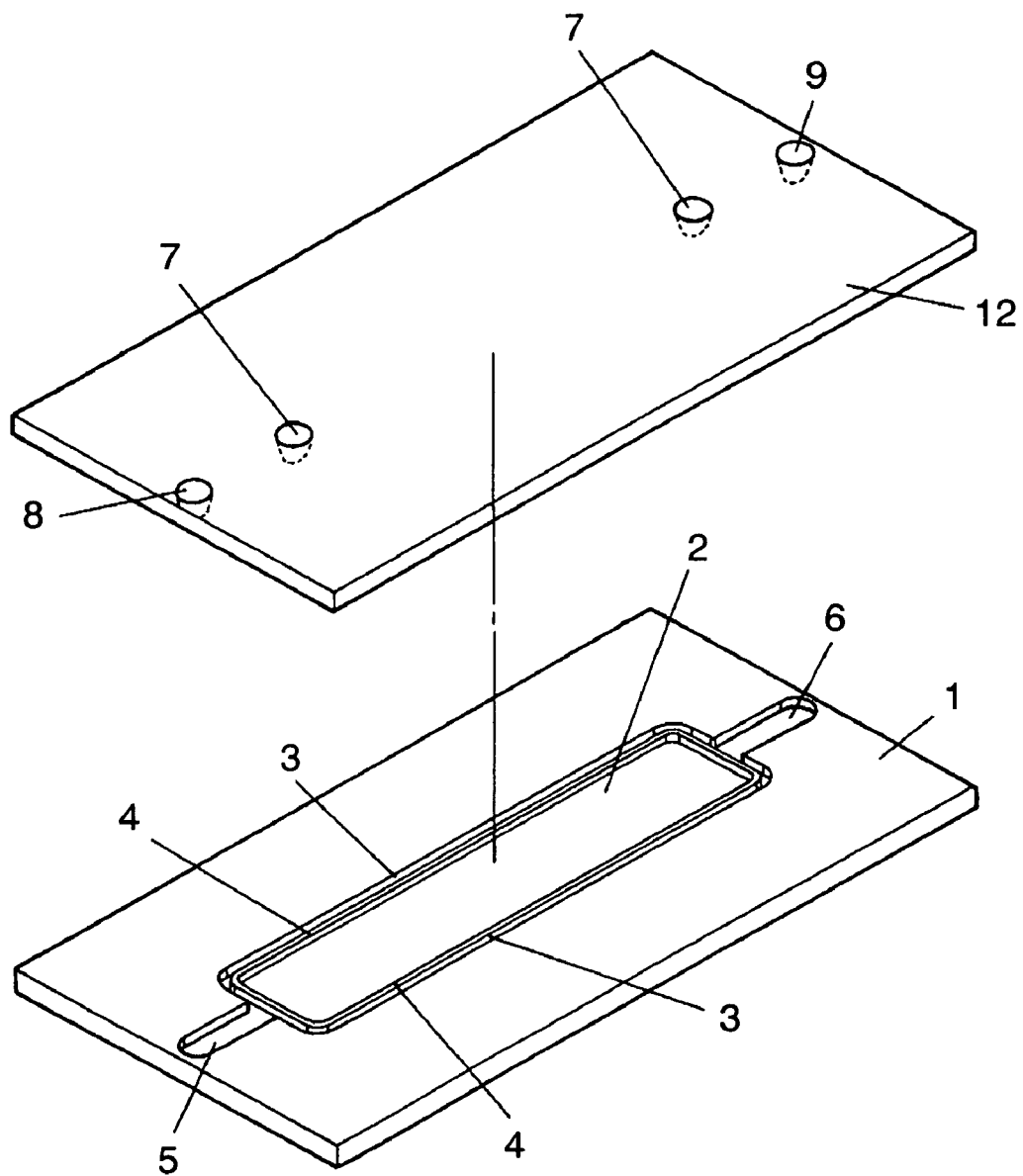
FIG. 1 is an exploded perspective view of a polymerase chain reaction kit of a first embodiment of the present invention.
Figure 2:
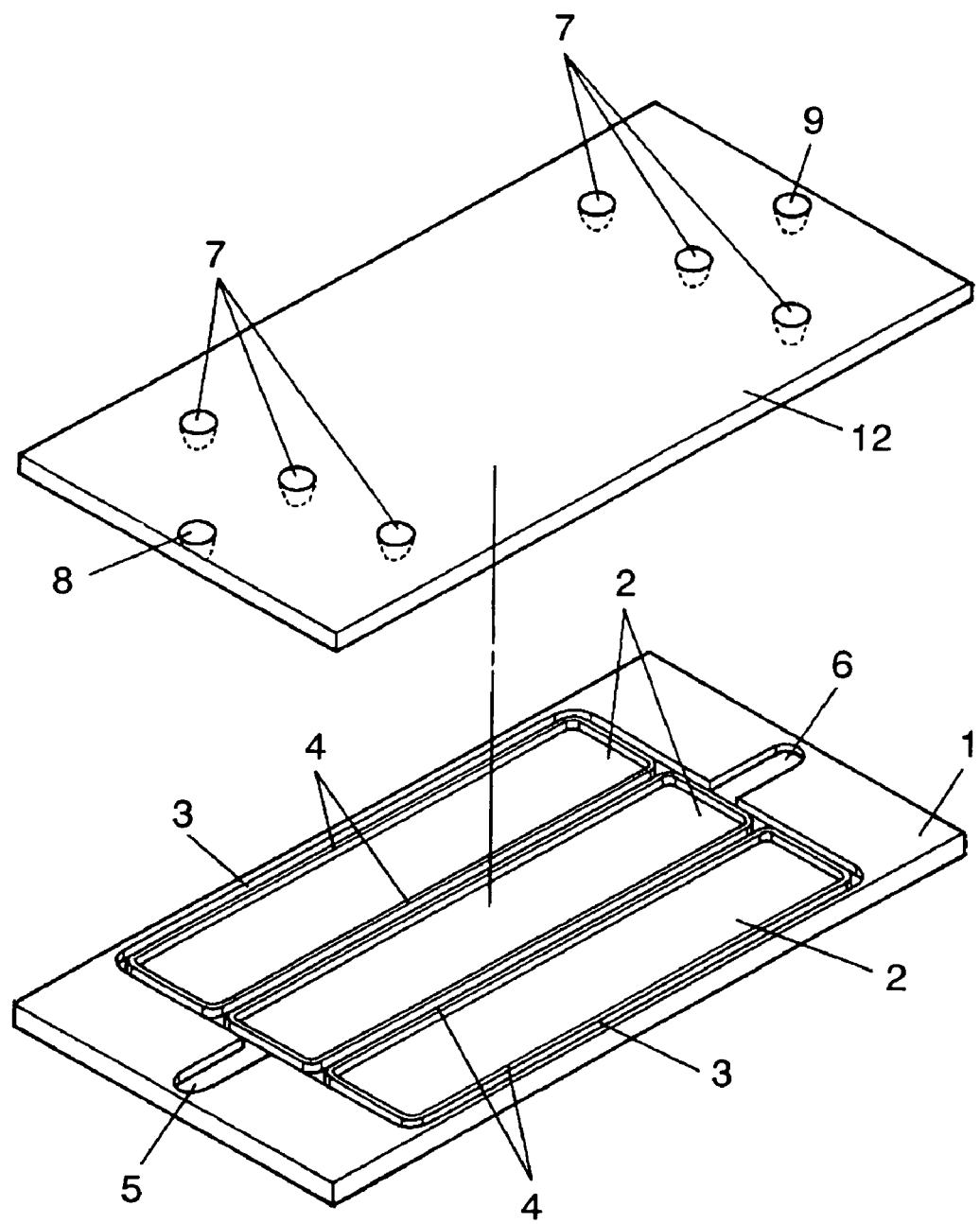
FIG. 2 is an exploded perspective view of another kit for polymerase chain reaction of the first embodiment.

FIG. 1 is an exploded perspective view of a polymerase chain reaction kit of a first embodiment. Substrate 1 made of silicon has cavity 2 on its first side. Flow channel 3 is formed along the both sides of cavity 2. Cavity 2 and flow channel 3 are separated by barrier 4 made of silicon.

Cavity 2 has a rectangular shape. Flow channel 3 is formed adjacent to longer sides of the rectangular. Flow channel 3 surrounds shorter sides of the rectangular to meet with flow-in groove 5 and flow-out groove 6.

In addition, cover plate 12 made of glass is attached with the first surface of substrate 1. Cover plate 12 has i) sample-injection inlets 7 to be connected with cavity 2 and ii) flow-in hole 8 and flow-out hole 9 for a heating medium to be connected with flow-in groove 5 and flow-out groove 6, respectively. Cover plate 12 seals cavity 2 and flow channel 3 from the outside, with only sample-injection inlets 7 (hereinafter, inlets 7), flow-in hole 8, and flow-out hole 9 exposed.

Substrate 1 made of silicon and cover plate 12 made of glass are directly attached or bonded with an adhesive. When an adhesive is used for bonding them, the adhesive may dissolve into a sample solution for the polymerase chain reaction in cavity 2. From the reason, the direct attachment should preferably be used. When it has no choice but to use an adhesive because of material constraints of substrate 1 and cover plate 12, a precaution against the adhesive mixing into the solution should be taken. Preferable attachment methods including the aforementioned direct attachment will be described later.

With the structure described above, cavity 2 can be filled with a sample solution with a minute quantity. That is, the polymerase chain reaction can be performed with minimum wastage of the sample solution. Besides, flow channel 3 is adjacent to at least a portion of cavity 2 via barrier 4. With such a structure, a heating medium circulating through the side surface of cavity 2 can provide the sample solution with a quick temperature control, thereby accelerating the polymerase chain reaction. In addition, barrier 4 as a separator between flow channel 3 and cavity 2 is made of silicon only—the same material as that of substrate 1. Forming cavity 2 and flow channel 3 from an identical base material can achieve a high-density arrangement in the structure. As another advantage, silicon material bears micromachining by the manufacturing method that will be described later. With the method, for example, barrier 4 can be thin to 100 μm or less. Barrier 4 is made of silicon, which has a thermal conductivity higher than the conductivity of glass and resin that have been employed for a prior-art structure. Moreover, barrier 4 is so thin. Therefore, when circulating through flow channel 3, the heating medium can rapidly increase or decrease the temperature of the sample solution in cavity 2.

Here will be described procedures of the polymerase chain reaction employing the polymerase chain reaction kit of the present invention.

Firstly, prepare a sample solution to be set in cavity 2. The sample solution is made of, for example, the mixture of materials below.

As a template of target DNA to be amplified, λDNA is used. As a primer, 5'-GATGAGTTCGTGTCCGTACAACT-3' (SEQ ID NO: 1) and 5'-GGTTATCGAAATCAGCCA-CAGCGCC-3' (SEQ ID NO: 2) are used. Their concentrations are controlled appropriately. It will be understood that A stands for the adenine base, G for the guanine base, C for the cytosine base, and T for the thymine base. Furthermore, an appropriate amount of other necessary components, such as polymerase, deoxynucleoside triphosphate mix, $MgCl_2$, are added to the material above to prepare the sample solution.

Next, inject the sample solution into cavity 2 through inlets 7 of the polymerase chain reaction kit shown in FIG. 1, and cover inlets 7 with a lid (not shown). Pressing silicon rubber and the like against inlets 7 can keep the sample solution from leakage. On the other hand, connecting flow-in hole 8 and flow-out hole 9 to an external heat circulator allows a heating medium to circulate through flow channel 3. In the heating process, heating media having three different temperatures of approx. 94° C., 55° C., and 72° C. are circulated in the order named for a predetermined period. Circulating the heating media provides the sample solution with a temperature suitable for each process of the polymerase chain reaction—encouraging i) thermal denaturation by the heating medium of 94° C., ii) annealing by the heating medium of 55° C., and iii) extension reaction by the heating medium of 72° C. The temperature-control cycle of i) through iii) is repeated 30 to 50 times. In this way, the target DNA is amplified by the polymerase chain reaction.

According to the polymerase chain reaction kit of the present embodiment as described above, the 3-step temperature control of the sample solution is done by circulating heating media heated appropriate for each process. Besides, barrier 4 made of silicon with a thickness of 100 μm or less is all that divides cavity 2 from flow channel 3. The structure therefore encourages a vigorous heat exchange. Compared to the structure in which a heating block is used for controlling the temperature of a sample solution, the structure of the present embodiment can extremely shorten the time required for the reaction processes.

Furthermore, cavity 2, which is minutely disposed in the first surface of substrate 1, ensures that the polymerase chain reaction takes place, even with a small quantity of a sample solution.

Inlet 7, flow-in hole 8 and flow-out hole 9 should preferably be formed into a conic shape, in which the diameter on the upper side of glass cover plate 12 is larger than the one on the side to be attached with substrate 1. Forming the holes conic facilitates injection of a sample solution with a micropipette and the like. As another advantage of the conical shape, a tube for circulating heating media can be easily inserted in flow-in hole 8 and flow-out hole 9. Although a sample solution can be injected/removed through a single inlet, it is preferable to have two or more injection inlets 7. When a sample solution is injected in one of the inlets, the rest can escape air from cavity 2, encouraging an easy injection. It will be understood that forming either one of inlet 7, flow-in hole 8 and flow-out hole 9 into a conic shape can have a preferable effect.

In addition, the rectangular shape of cavity 2 allows the structure to have a high-density arrangement in which a plurality of cavities 2 are located adjacent to each flow channel 3. By virtue of the structure, the kit of the present embodiment can handle more than one sample solution for the polymerase chain reaction at a time. Furthermore, each cavity 2 may be filled with a sample solution containing different target DNA for amplifying more than one different target DNA. Providing each sample solution with temperature control by circulation of a heating medium allows the kit to separately carry out the polymerase chain reaction with respect to each sample solution. Instead of the rectangular shape, oval-shaped cavity 2 is also able to offer the same effect.

Figure 3:
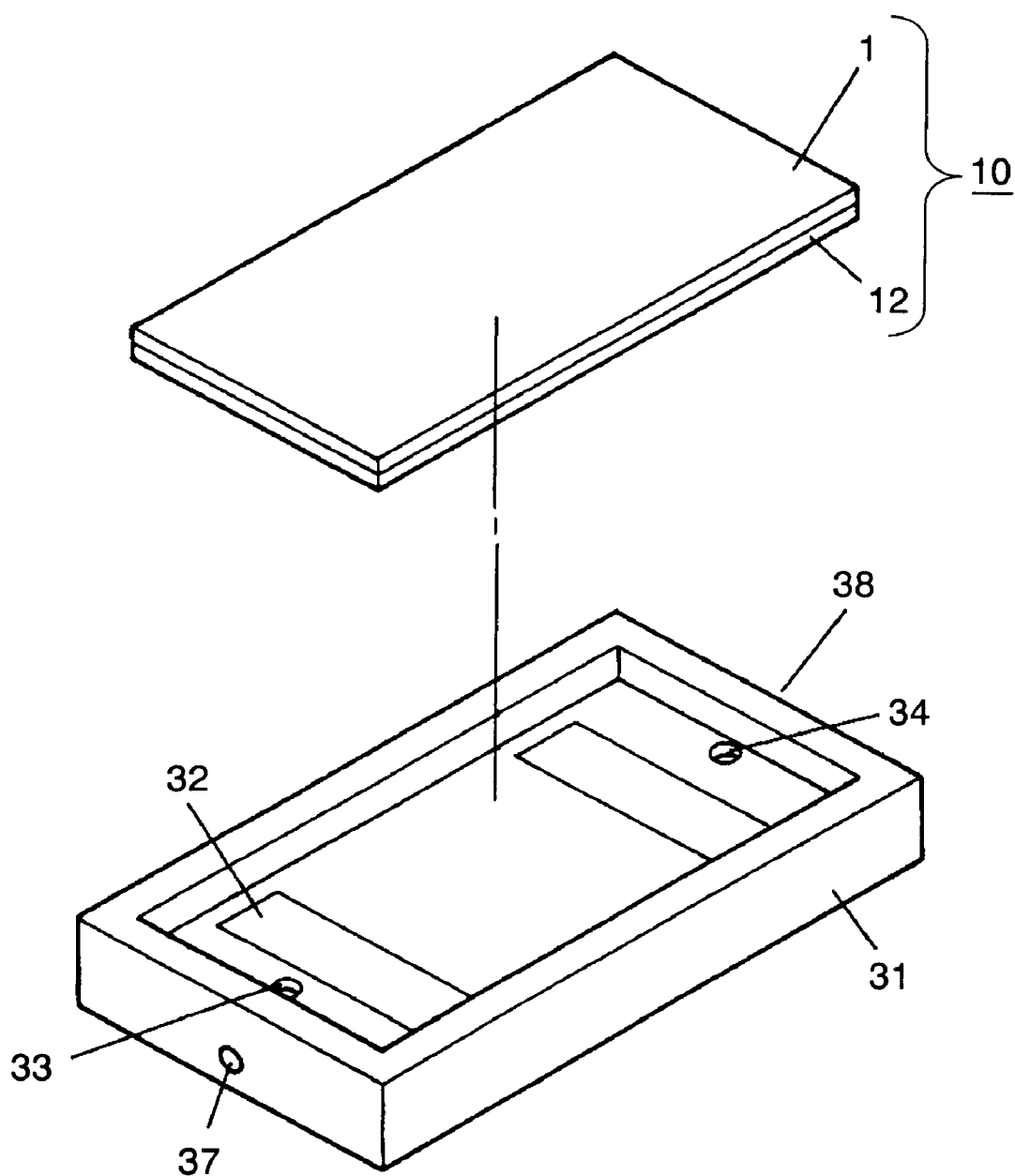
FIG. 3 is a perspective view of the polymerase chain reaction kit of the first embodiment and an attachment plate that accept the kit.

Besides, the structure, in which inlet 7, flow-in hole 8 and flow-out hole 9 are all disposed on the top surface of cover plate 12, can simplify the process of circulating a heating medium. Here will be an explanation in some detail, using attachment plate (hereinafter, plate) 31 shown in FIG. 3. Plate 31 has a recess in which polymerase chain reaction kit 10 (hereinafter, kit 10) of the embodiment is to be accommodated. Cover sheet 32 made of silicone rubber is disposed at a section corresponding to inlet 7 of kit 10. In addition, feed-in hole 33 and feed-out hole 34 are disposed so as to correspond to flow-in hole 8 and flow-out hole 9, respectively. Furthermore, external inlet 37 and external outlet 38 of plate 31 are connected in fluid communication to feed-in hole 33 and feed-out hole 34, respectively.

In such structured kit 10 in which inlet 7, flow-in hole 8 and flow-out hole 9 are all disposed on the same surface of cover plate 12, a sample solution is injected into cavity 2 and then kit 10 is set in plate 31 so as to face cover plate 12 to plate 31. Through the set-in, the sealing of inlet 7, the connection between flow-in hole 8 and feed-in hole 33, and the connection between flow-out hole 9 and feed-out hole 34 can be simultaneously done, whereby the operations required for the reaction process can be simplified. Forming either one of inlet 7, flow-in hole 8, and flow-out hole 9 disposed on cover plate 12 enables one of the sealing and the connections described above.

Figure 4:
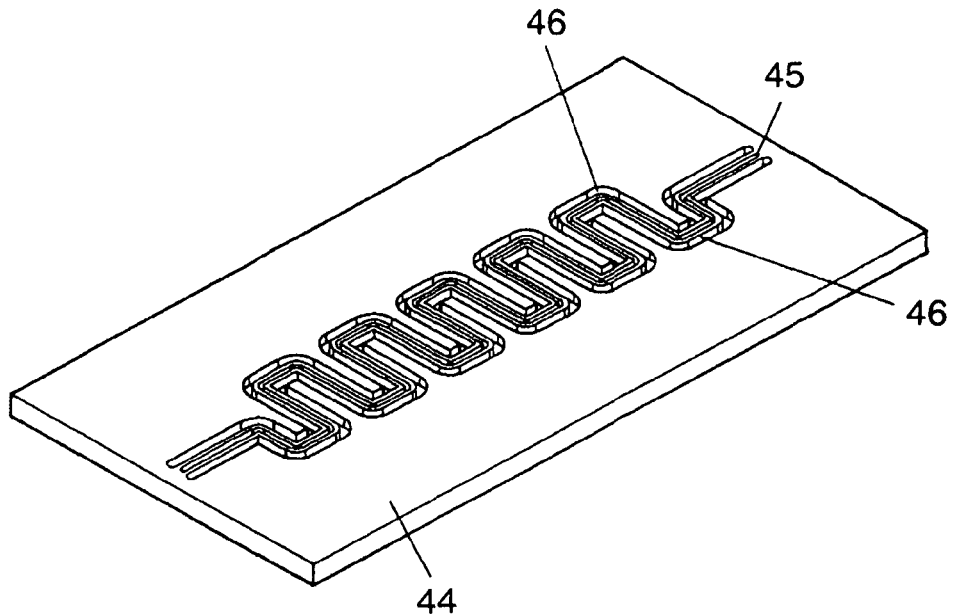
FIG. 4 is a perspective view of still another kit for the polymerase chain reaction of the first embodiment.

Although the cavity described in the embodiment has a rectangular shape, it is not limited thereto, as long as high thermal conduction between the cavity and the flow channel can be maintained. The cavity may be formed into, for example, the structure shown in FIG. 4. Cavity 45 formed on substrate 44 has a meander shape with a narrow width and a plurality of bends. Flow channel 46 runs along both sides of cavity 45. The structure, in which flow-channel 46 has a large area with respect to the volume of cavity 45, allows a heating medium to provide a sample solution with an effective temperature control.

Forming the cavity so as to have a narrow width enhances thermal efficiency. Furthermore, forming the cavity so as to have many bends realizes a high-density mounting on the substrate. Therefore, a spiral cavity can provide the same effect.

Here will be described the process of manufacturing the polymerase chain reaction kit of the embodiment with reference to the drawings. FIGS. 5 through 9 are sectional views illustrating the process of manufacturing the polymerase chain reaction kit of the embodiment.

Figure 5:
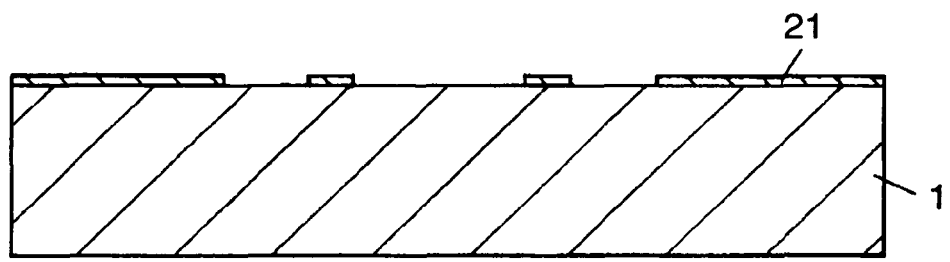
FIGS. 5 through 9 show sectional views illustrating the manufacturing steps of the polymerase chain reaction kit of the first embodiment.

Resist mask 21 is formed on substrate 1 made of silicon, as shown in FIG. 5, by photolithography. When substrate 1 and a glass plate are to be fixed by the direct attachment, at least the upper surface of substrate 1 has to be polished in advance into a mirror surface; the polishing is no need for other attachment method.

Figure 6:
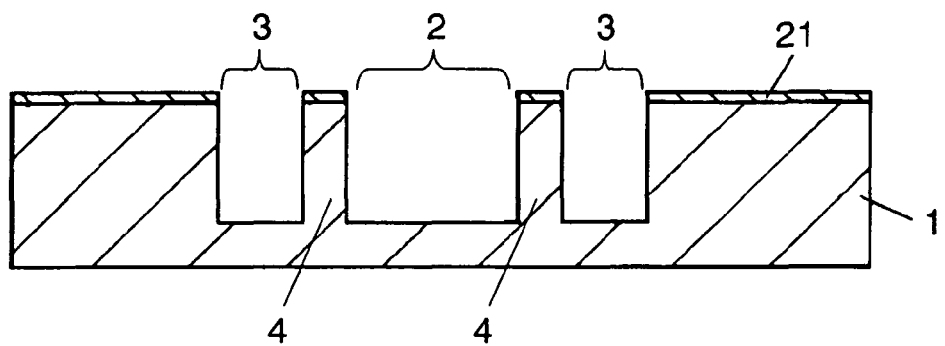

Next, cavity 2 and flow channel 3 are formed by etching, as shown in FIG. 6. The etching process should preferably be performed through dry etching with at least two kinds of gases: a promotive gas and a suppressive gas for etching. In the etching process employing promotive gas, such as $SF_6$, and $CF_4$, the etching intrudes under resist mask 21—known as the side-etch phenomenon. It is therefore impossible to have etched grooves with high density. On the other hand, in the etching process in which suppressive gases such as $C_4F_8$ and $CHF_3$ are mixed into the aforementioned promotive gases, the etching proceeds downward only. It is because of a protective film formed on an etched edge by the suppressive gas. This allows the substrate to have a precise configuration of cavity 2 and flow channel 3.

In the etching process, it is preferable that the operation of 1-3 μm etching by the promotive gas and the operation of forming 0.3-1 μm protective film by the suppressive gas should be alternatively repeated every few seconds. Compared to the use with the two gases mixed, the alternate use of the two gases can form barrier 4 with higher verticality, allowing the substrate to have cavity 2 and flow channel 3 thereon with maximum density. Although the description above suggests 1-3 μm etched-away amount of the substrate and 0.3-1 μm thickness of the protective film, it is not limited thereto; they can be properly determined according to the configuration of cavity 2 and channel 3.

Figure 7:
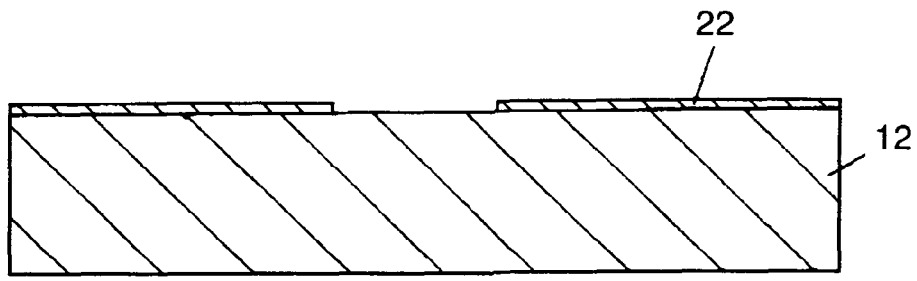

Next, resist mask 22 is formed, as shown in FIG. 7, on cover plate 12 made of glass. When cover plate 12 and substrate 1 are to be fixed by the direct attachment, at least the lower surface of cover plate 12 has to be mirror-finished; the mirror plane is no need for other attachment method.

Figure 8:
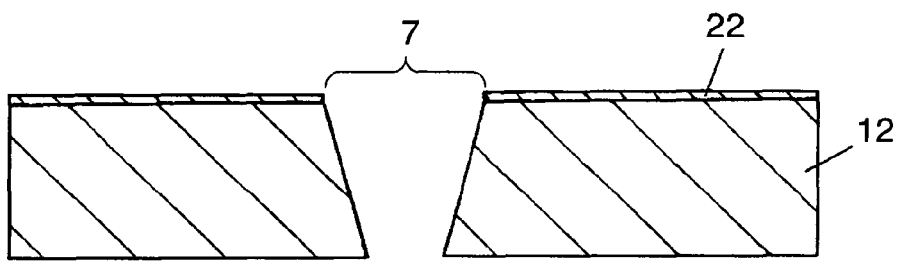

Following the process above, inlet 7, flow-in hole 8 and flow-out hole 9 (both holes are not shown) are formed in cover plate 12 by sand blasting. Employing the sand blasting can form these holes into conical, as shown in FIG. 8. Such a conical hole facilitates an easy injection of a heating medium or a sample solution by a micropipette as described above.

Figure 9:
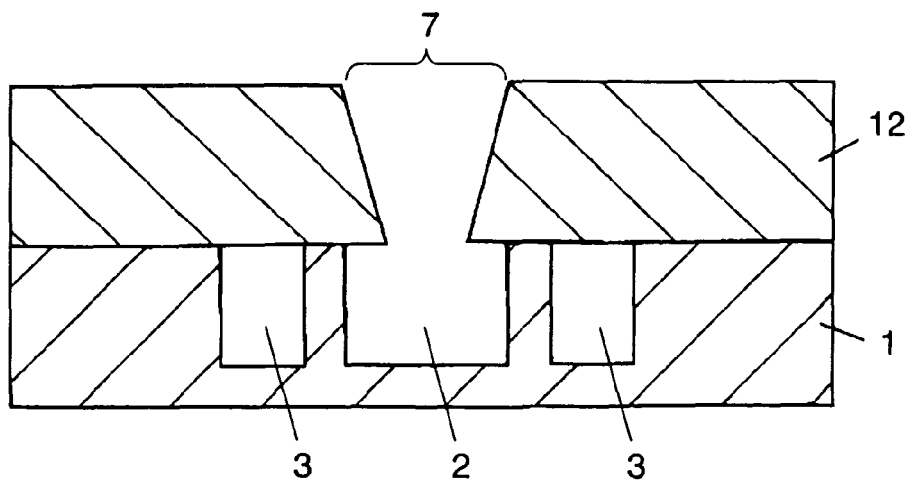

Attaching surfaces of substrate 1 and cover plate 12 is thoroughly cleansed, with a careful handling, to be free from dirt. As shown in FIG. 9, pressing the surfaces against with each other so as to remove air therebetween generates an attractive force, i.e., van der Waals force between substrate 1 and cover plate 12. Through the application of heat ranging from 250° C. to 500° C., substrate 1 and cover plate 12 are given a secure bond. In this way, the direct attachment completes the polymerase chain reaction kit of the embodiment.

It is also possible of forming a plurality of the kits on a large substrate at a time. In this case, substrate 1 and cover plate 12 are attached together through the direct attachment, and then separated into individual kits by dice cutting. As another effective bonding, substrate 1 and cover plate 12 can be bonded by an anodic attachment. In the anodic attachment, the application of high voltage provides substrate 1 and cover plate 12 with an electrical adsorption after pressing substrate 1 and cover plate 12 against with each other. Furthermore, through the application of heat of 250-500° C., substrate 1 and cover plate 12 have a secure bond. Other than the aforementioned attachment methods, the two plates can be bonded with an adhesive. In this case, a precaution against the material of the adhesive having any negative effect on the sample solution should be taken.

Substrate 1 can be made of other material than silicon, as long as the material has no chemical reaction with the sample solution: semiconductor such as gallium arsenide, glass, plastics, ceramics, metal, etc. The glass substrate may include silica glass, lead glass, boro-silicated glass, soda glass. The plastics substrate may include polymethyl methacrylate and its copolymer, polystylene, polyethylene terephthalate. Substrate 1 made of gallium arsenide is etched, for example, through dry etching such as reactive ion etching (RIE). Glass substrate 1 may be etched by wet etching containing fluoric acid, as well as the dry etching. Plastics substrate 1 may be processed by nano-printing; but still, silicon is the most superior material for substrate 1 in providing a minute cavity with high precision with the etching method described above.

On the other hand, cover plate 12, which prevents a sample solution from leakage out of cavity 2, can be formed of material the same as that of substrate 1. In the bonding process, cover plate 12 and substrate 1 need to have an intimate contact to seal the sample solution in cavity 2. Therefore, it is important to select the material combination suitable for the bonding between substrate 1 and cover plate 12. For example, for non-adhesive bonding including the anodic attachment and the direct attachment, the preferable combination is: i) substrate 1 made of silicon and cover plate 12 made of silicon dioxide or a glass containing silicon dioxide, ii) substrate 1 made of silicon and cover plate 12 made of silicon, or iii) glass substrate 1 and glass cover plate 12. Other than the aforementioned material selection, there are many applicable combinations, for example, the combination commonly made of crystal, the combination commonly made of lithium tantalate.

As still another bonding, fluoric acid bonding can be employed. In the bonding, the application of fluoric acid to the attached surfaces of substrate 1 and cover plate 12 melts the boundary area, providing a secure bond. In this case, the material combination commonly made of glass, or silica glass is employed. For a bonding with adhesives, the material may be made of plastics. As described above, there are various material combinations; an optimal combination should be determined according to the following points: a bonding method, a processing method of cavity 2 and channel 3, required cavity-density, thermal conductivity of material, and costs.

Silicon substrate 1 and glass cover plate 12 described in the embodiment is one of the excellent combination in terms of i) having cavity 2 in high-density array, ii) high thermal conductivity of silicon, and iii) a reliable bonding.

Second Exemplary Embodiment

Figure 10:
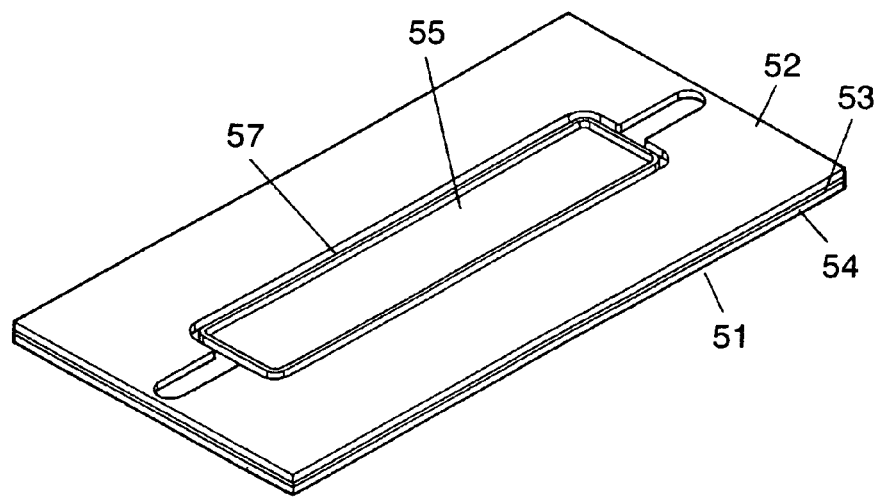
FIG. 10 is an exploded perspective view of the substrate of the polymerase chain reaction kit of a second embodiment.
Figure 11:
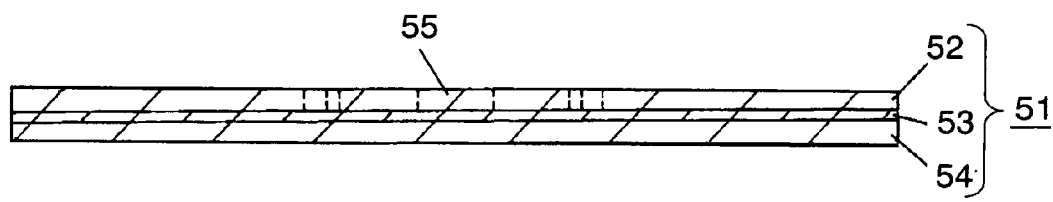
FIG. 11 is a sectional view of the substrate of the polymerase chain reaction kit shown in FIG. 10.

FIG. 10 is an exploded perspective view of the substrate of the polymerase chain reaction kit of a second embodiment. FIG. 11 is a side view of the kit shown in FIG. 10. The structure of the embodiment differs from the structure of the first embodiment in that substrate 51 has a multi-layered structure formed of silicon layers 52, 54, and glass plate 53 made of silicon dioxide or glass containing silicon dioxide.

In the first embodiment, the substrate is formed of silicon only. To provide a consistent depth of cavity 2 shown in FIG. 1, it is necessary to stop the etching operation at a predetermined etching depth. An etching rate, however, depends on the operating condition of an etching device, accordingly, it is often difficult to stop the operation at a desired depth. Generally, in manufacturing polymerase chain reaction kit 10, because of its tiny body with approx. 5×10 mm, a plurality of cavities 2 are etched in a silicon substrate with a diameter more than 100 mm by etching. In this case, the cavities variously located in the substrate may not have a uniform etching depth due to variations in etching devices or etching conditions.

To address the problem above, substrate 51 of the embodiment has a multi-layered structure formed of silicon layers 52, 54, and glass plate 53 made of silicon dioxide or glass containing silicon dioxide. In the etching process, only upper silicon layer 52 is etched. That is, as shown in FIG. 11, cavity 55 has a depth corresponding to the thickness of silicon layer 52, keeping a uniform etching depth. As described above, employing multi-layered substrate 51 can provide a highly accurate configuration of a cavity, a flow channel, and a barrier, thereby allowing the polymerase chain reaction kit to have quite a consistent amount of a sample solution.

Figure 12:
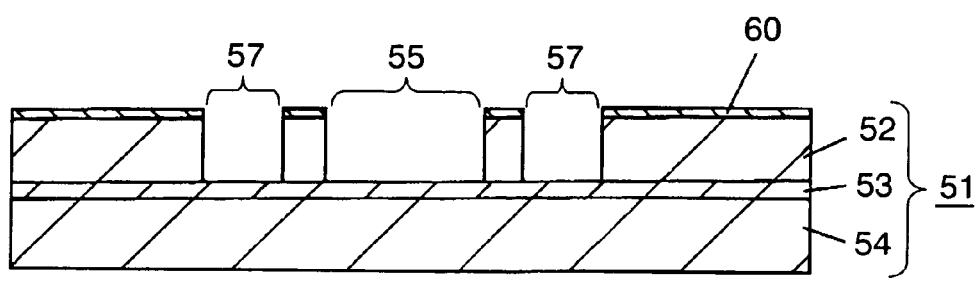
FIGS. 12 and 13 show sectional views illustrating manufacturing steps of the polymerase chain reaction kit of the second embodiment.

Here will be given more in-detail explanation of manufacturing the kit, with reference to FIGS. 12 and 13.

First, resist mask 60 is formed on the side of upper silicon layer 52 of substrate 51 by photolithography. Cavity 55 and flow channel 57 are formed, as shown in FIG. 12, through dry etching. The dry etching is carried out in the same manner as that described in the first embodiment. The etching rate perceptibly slows down when the etching depth reaches the surface of glass plate 53. That is, the thickness of upper silicon layer 52 defines the depth of a cavity, allowing each cavity to have a uniform depth.

Figure 13:
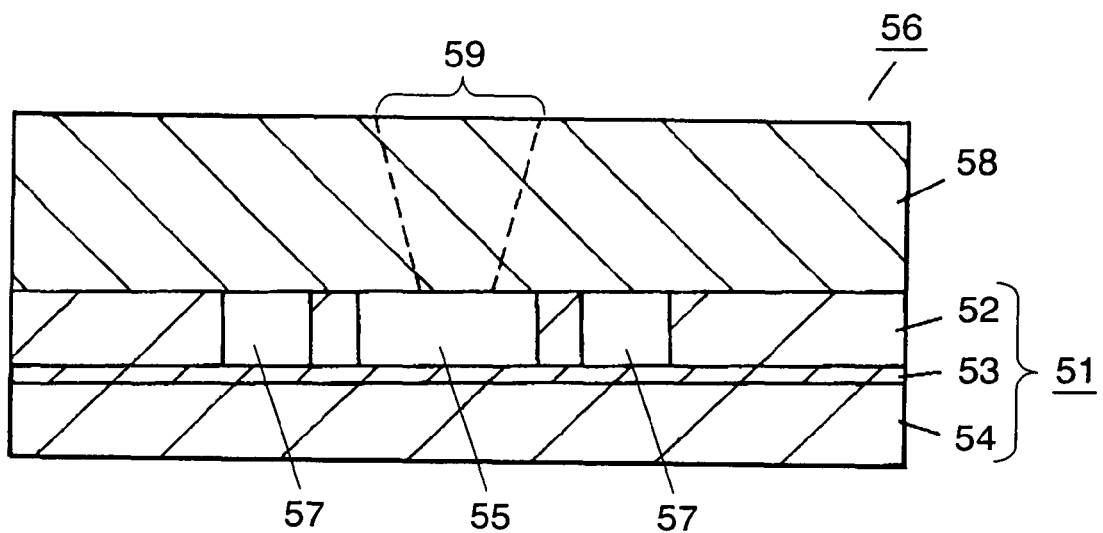

Next, as shown in FIG. 13, glass cover plate 58 having sample injection inlet 59, a flow-in hole and a flow-out hole (both the holes are not shown), is attached on a first surface of substrate 51. This completes polymerase chain reaction kit 56 of the embodiment.

Injection inlet 59, the flow-in and flow-out holes are exactly alike to those introduced in the first embodiment in term of the manufacturing method, the positioning, and the shape. Like the structure in the first embodiment, forming the openings into a conical shape enhances an easy injection of a sample solution and a heating medium. In addition, disposing the holes to cover plate 58 is effective in that the sample solution can be easily set in cavity 55 and the heating medium can be easily put into, and collected from channel 57.

Third Exemplary Embodiment

Figure 14:
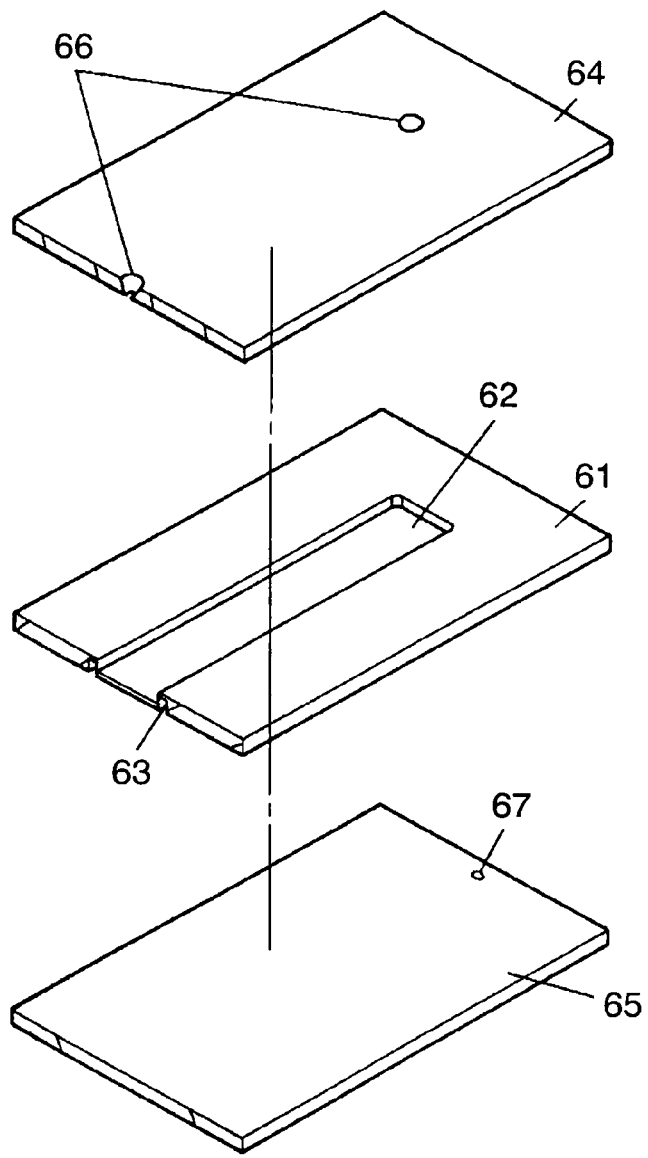
FIG. 14 shows an exploded perspective view, which is cut at a section, of the polymerase chain reaction kit of a third embodiment.
Figure 15:
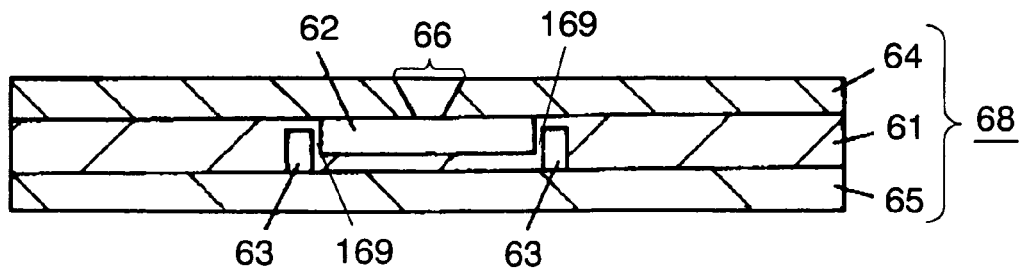
FIG. 15 is a sectional view of the polymerase chain reaction kit shown in FIG. 14.

FIG. 14 shows an exploded perspective view, which is cut at a section, of polymerase chain reaction kit 68 of a third embodiment. FIG. 15 is a sectional view of the kit shown in FIG. 14. For sake of clarity, both the figures show the sections taken at sample injection inlet 66 (hereinafter, inlet 66). Cavity 62 is formed, as shown in FIG. 14, on a first surface of substrate 61. Flow channel 63 is disposed on a second surface of substrate 61 so as to run along side section 169 of cavity 62. Substrate 61 is sandwiched between first cover plate 64 having inlet 66 and second cover plate 65 having a flow-in hole (not shown) and flow-out hole 67 for a heating medium. Serving as a barrier, side section 169 separates cavity 62 containing a sample solution from channel 63 through which a heating medium circulates. Therefore, the structure is free from the worry that the sample solution could mix with the heating medium.

In the structure of the first embodiment shown in FIG. 1, cavity 2 and flow channel 3 are divided by attaching cover plate 12 with barrier 4. When a gaseous fluid, such as He, $N_2$, is employed for a heating medium, such structured kit can cause a problem—if flow channel 3 has a minor defect due to poor attachment, the gaseous fluid could escape through the clearance into cavity 2. On the other hand, the kit of the third embodiment provides a complete separation between the sample solution and the heating medium, accordingly, such inconveniencies will never occur.

Figure 16:
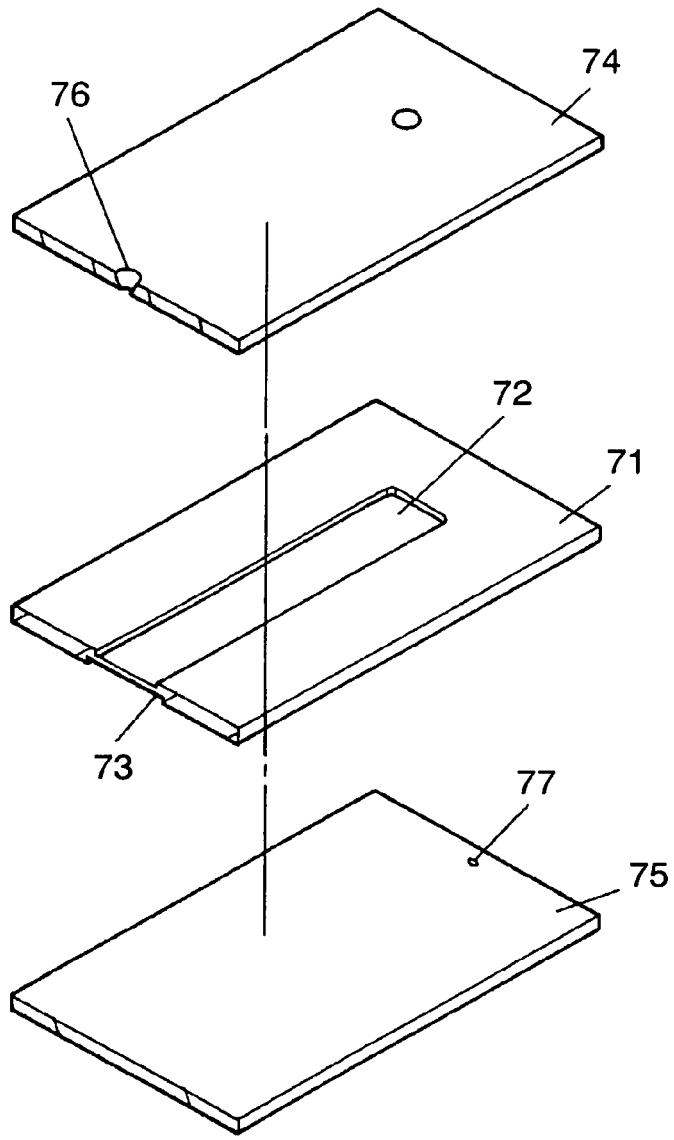
FIG. 16 shows an exploded perspective view, which is cut at a section, of another kit for the polymerase chain reaction of the third embodiment.
Figure 17:
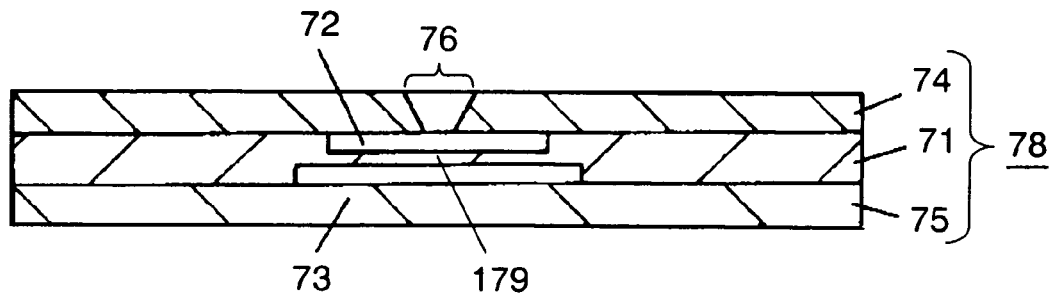
FIG. 17 is a sectional view of the polymerase chain reaction kit shown in FIG. 16.

Here will be described a still further structure of the embodiment. FIG. 16 shows an exploded perspective view, which is cut at a section, of polymerase chain reaction kit 78 of the embodiment. FIG. 17 is a sectional view of the kit shown in FIG. 16. For sake of clarity, both the figures show the sections taken at sample injection inlet 76 (hereinafter, inlet 76).

Cavity 72 is formed, as shown in FIG. 16, on a first surface of substrate 71. Flow channel 73 is disposed on a second surface of substrate 71 so as to run along bottom section 179 of cavity 72. Like the structure earlier described in the embodiment, substrate 71 is sandwiched between first cover plate 74 having inlet 76 and second cover plate 75 having a flow-in hole (not shown) and flow-out hole 77 for a heating medium. Serving as a barrier, bottom section 179 completely separates cavity 72 containing a sample solution from channel 73 through which a heating medium circulates. The structure in which the flow channel runs beneath the cavity allows flow channel 73 to have larger area to cover largely formed cavity 72. With such a structure, the heating medium circulating through flow channel 73 can control, with reliability, the temperature of the sample solution in cavity 2. The width of flow channel 73 should preferably be greater, as shown in FIG. 17, than bottom section 179 of cavity 72. Such a structure contributes to an effective heat exchange through the entire area of bottom section 179, as well as helping an easy formation of flow channel 73.

Figure 18:
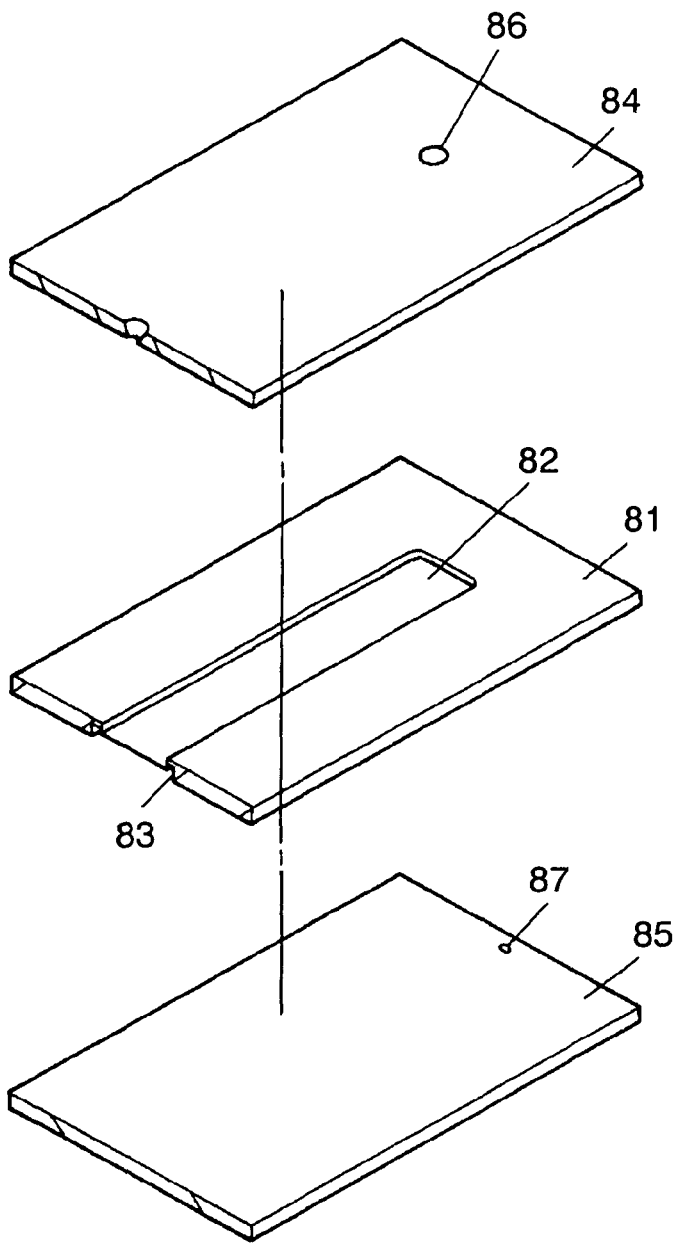
FIG. 18 shows an exploded perspective view, which is cut at a section, of still another kit for the polymerase chain reaction of the third embodiment.
Figure 19:
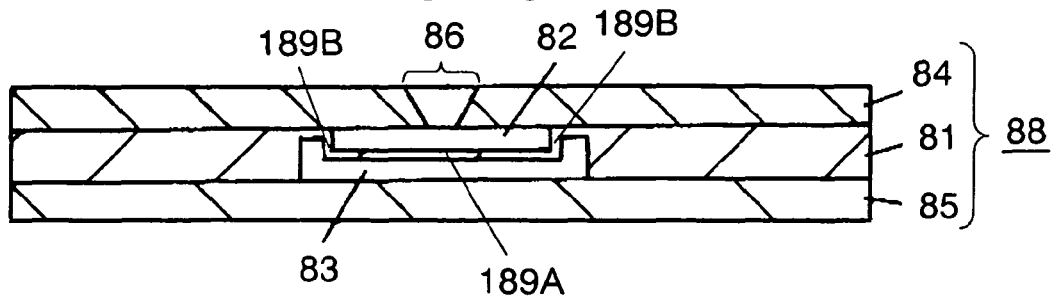
FIG. 19 is a section view of the polymerase chain reaction kit shown in FIG. 18.

Here will be described a yet further structure of the embodiment. FIG. 18 shows an exploded perspective view, which is cut at a section, of polymerase chain reaction kit 88 of the embodiment. FIG. 19 is a sectional view of the kit shown in FIG. 18. For sake of clarity, both the figures show the sections taken at sample injection inlet 86 (hereinafter, inlet 86).

Cavity 82 is formed, as shown in FIG. 18, on a first surface of substrate 81. Flow channel 83 is disposed on a second surface of substrate 81 so as to run along bottom section 189A and side section 189B of cavity 82. Like the structure earlier described in the embodiment, substrate 81 is sandwiched between first cover plate 84 having inlet 86 and second cover plate 85 having a flow-in hole (not shown) and flow-out hole 87 for a heating medium. Like the aforementioned two structures, cavity 82 containing a sample solution and flow channel 83 are completely separated by a barrier formed of bottom section 189A and side section 189B. The structure, in which flow channel 83 runs along the side and the bottom of cavity 82, allows flow channel 83 to surround cavity 82 with larger area in the case of cavity 82 with larger area. Such a structure further enhances heat exchange between a sample solution and a heating medium.

According to the structures in the embodiment, a sample solution undergoes the chain reaction in cavities 62, 72, and 82. With the structures above, the cavity can be filled with a sample solution with a minute quantity. That is, the polymerase chain reaction can be performed with minimum wastage of the sample solution. Besides, flow channels 63, 73, and 83 are adjacent to at least a portion of cavities 62, 72, and 73 via barriers 169, 179, and 189A, 189B, respectively. With such a structure, a heating medium circulating along the side section, the bottom section, or both sections of cavities 62, 72, and 82 can provide the sample solution with a quick temperature control, thereby accelerating the polymerase chain reaction. In addition, the sample solution and the heating medium are completely separated in all cases above.

Next will be described the procedures of manufacturing polymerase chain reaction kits 68, 78, and 88 of the embodiment with reference to the drawings.

To begin with, the procedure of manufacturing kit 68 of FIG. 14 will be described with reference to FIGS. 20 through 22.

Figure 20:
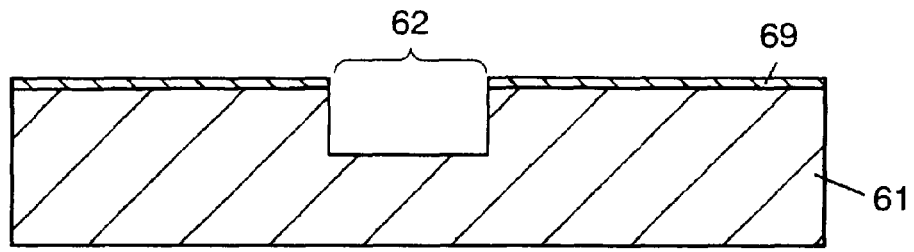
FIGS. 20 through 22 are sectional views illustrating the manufacturing steps of the polymerase chain reaction kit shown in FIG. 14.
Figure 21:
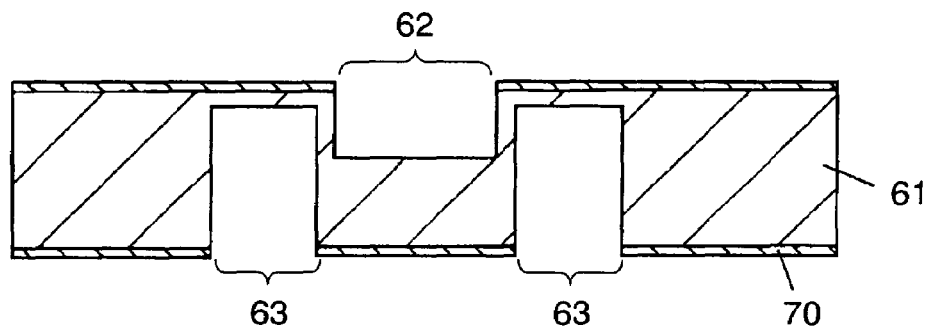

Cavity 62 is formed, as shown in FIG. 20, on the first surface of silicon substrate 61. The forming process is the same as that described in the first embodiment; forming resist mask 69 by photolithography, and then forming cavity 62 through dry etching using a suppressing gas and a promotive gas for etching.

As the next step, resist mask 70 is formed on the second surface of substrate 61 by photolithography so as to run along both side sections of cavity 62, and then flow channel 63 is formed through dry etching. In the process, finishing the etching operation at an appropriate depth is needed so as not to etch through substrate 61.

The following process is similarly done to that of the first embodiment. That is, inlet 66 is formed in first glass cover plate 64, on the other hand, the flow-in hole and flow-out hole 67 are formed in second glass cover plate 65. The holes are formed by sand blasting. Attaching the two cover plates to silicon substrate 61 completes polymerase chain reaction kit 68. Inlet 66, the flow-in hole, and flow-out hole 67 are exactly alike to those of the first embodiment in terms of the forming process, the shape, and the effect to be expected.

Now will be described the manufacturing process of kit 78 shown in FIG. 16 with reference to FIGS. 23 and 24.

Figure 23:
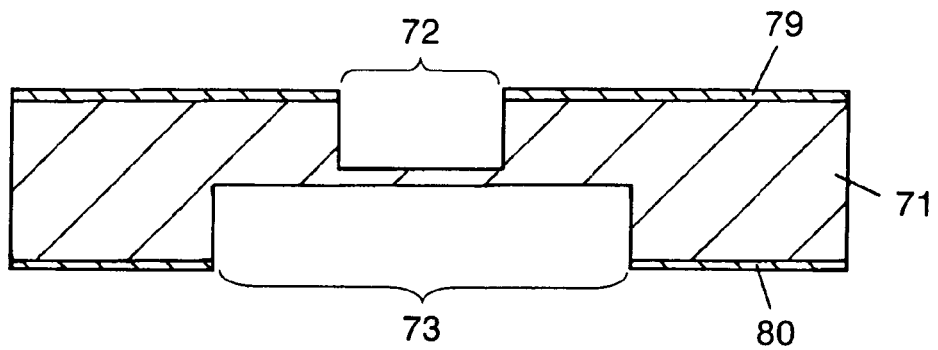
FIGS. 23 and 24 are sectional views illustrating the manufacturing steps of the polymerase chain reaction kit shown in FIG. 16.
Figure 24:
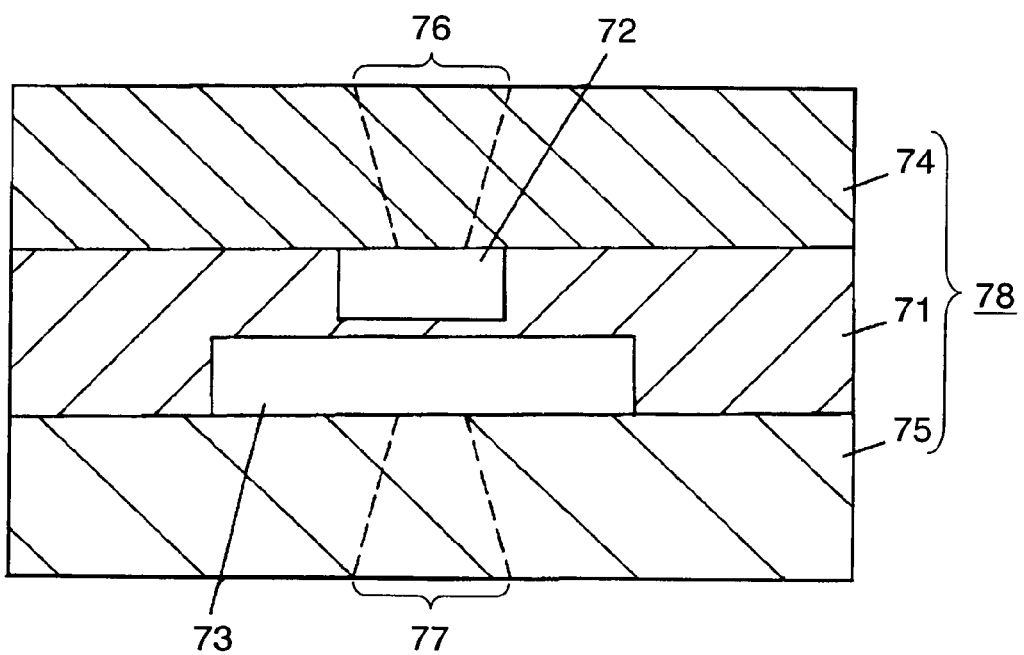

Firstly, using photolithography, resist mask 79 is formed on the first surface of substrate 71, as shown in FIG. 23, and then cavity 72 is formed through dry etching. And flow channel 73 is formed along the bottom of cavity 72. After resist mask 80 is formed also by photolithography, flow channel 73 is formed through dry etching. In this process, great care should be taken not to etch through the bottom of cavity 72.

Figure 22:
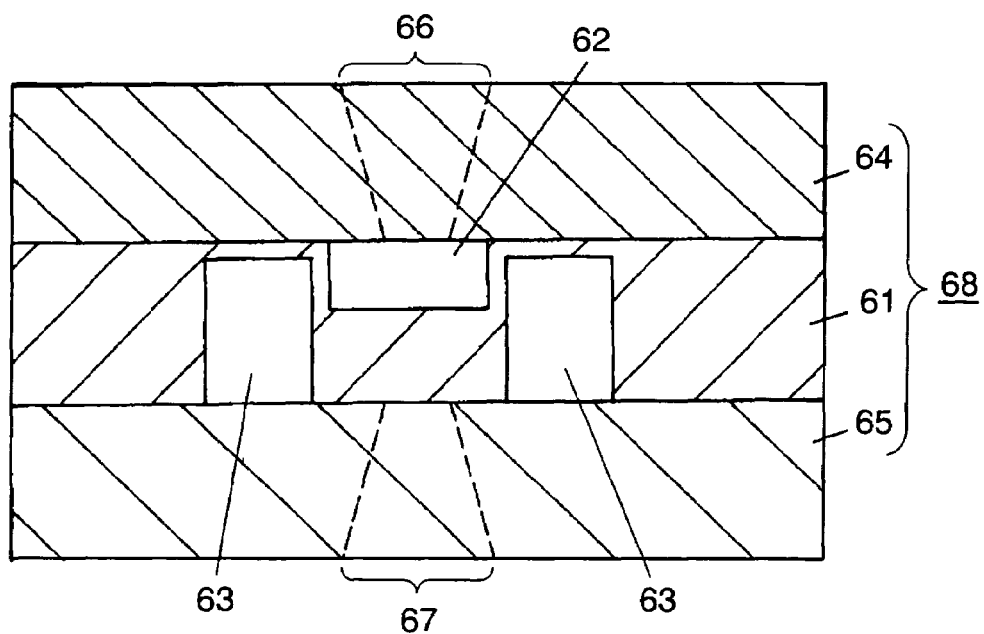

Next, as is the case shown in FIG. 22, first cover plate 74 having inlet 76 and second cover plate 75 having a flow-in hole and flow-out hole 77 are attached so as to sandwich substrate 71 therebetween. This completes polymerase chain reaction kit 78.

Figure 25:
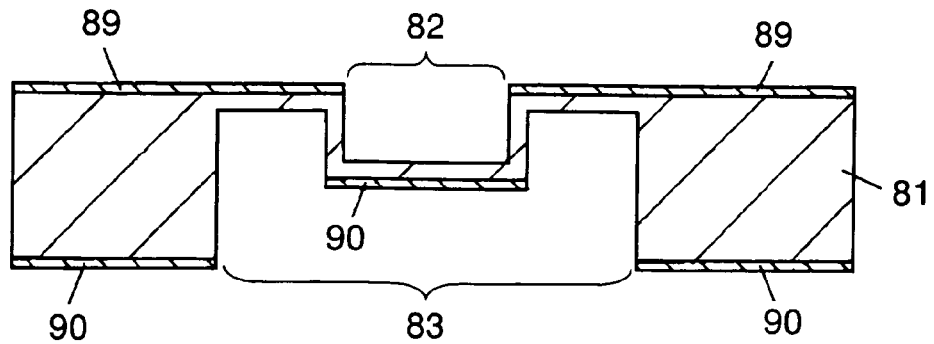
FIGS. 25 and 26 are sectional views illustrating the manufacturing steps of the polymerase chain reaction kit shown in FIG. 18.
Figure 26:
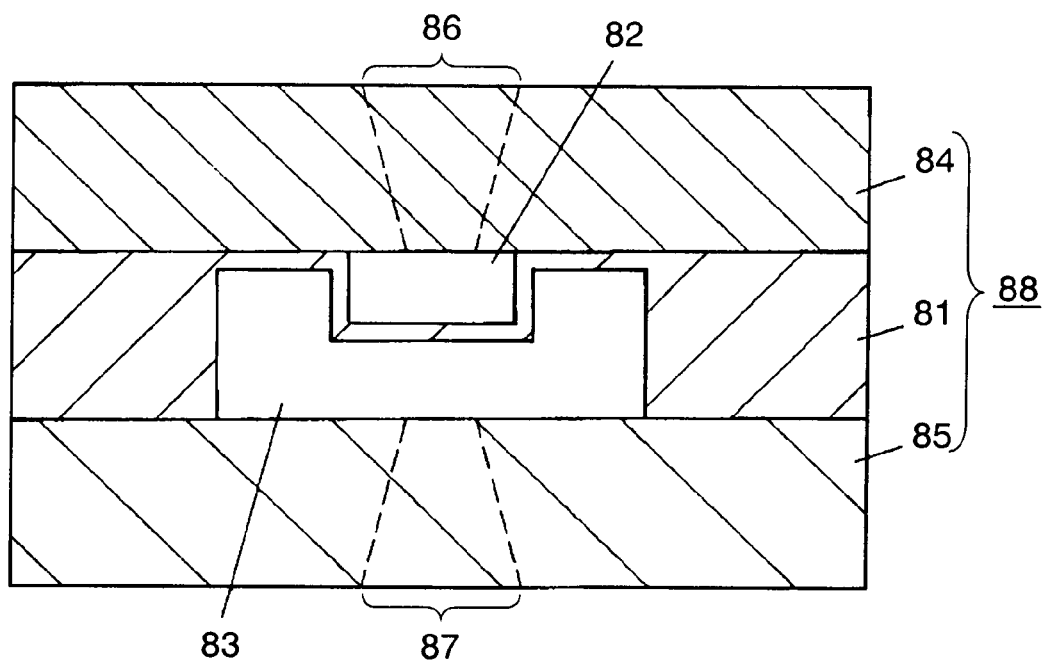

Turning now to FIGS. 25 and 26, the manufacturing process of kit 88 will be described.

Firstly, using photolithography, resist mask 89 is formed on the first surface of substrate 81, as shown in FIG. 25, and then cavity 82 is formed through dry etching. And flow channel 83 is formed along the side and bottom sections of cavity 82. As the first step of forming the flow channel, flow channel 73 is formed along the bottom, as is the case shown in FIG. 23. Next, resist mask 90 is formed, as shown in FIG. 25, on the bottom of cavity 82, and then the etching is performed along the side sections of cavity 82. In this way, intended flow channel 83 completes.

FIG. 26 shows the following process, that is, as is the case shown in FIG. 22, first cover plate 84 having inlet 86 and second cover plate 85 having a flow-in hole and flow-out hole 87 are attached so as to sandwich substrate 81 therebetween. This completes polymerase chain reaction kit 88.

Figure 27:
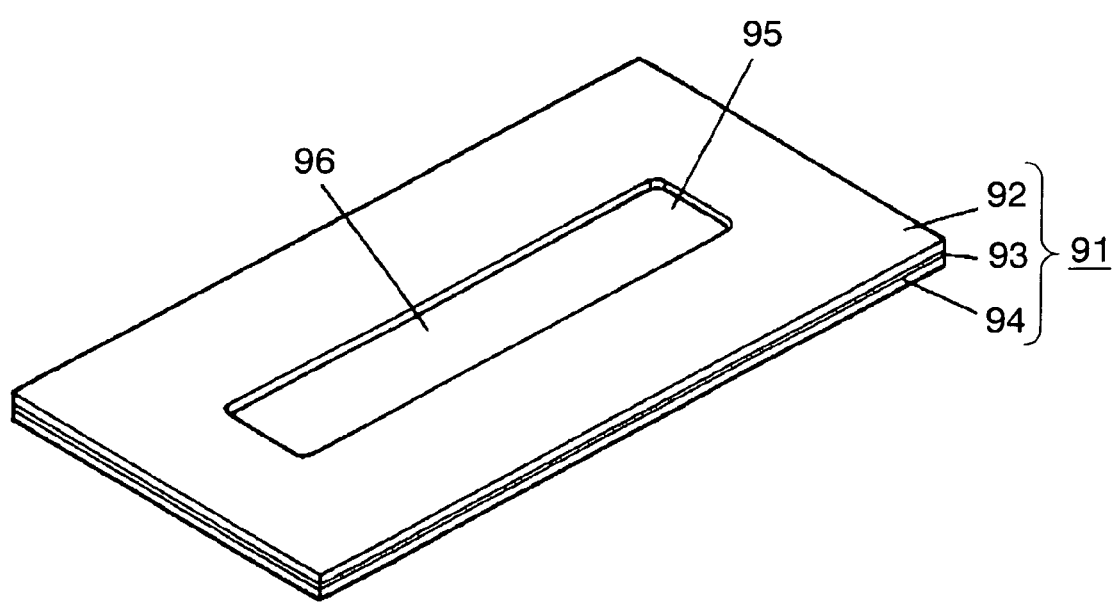
FIG. 27 is a perspective view of the substrate of still another kit for the polymerase chain reaction of the third embodiment.
Figure 28:
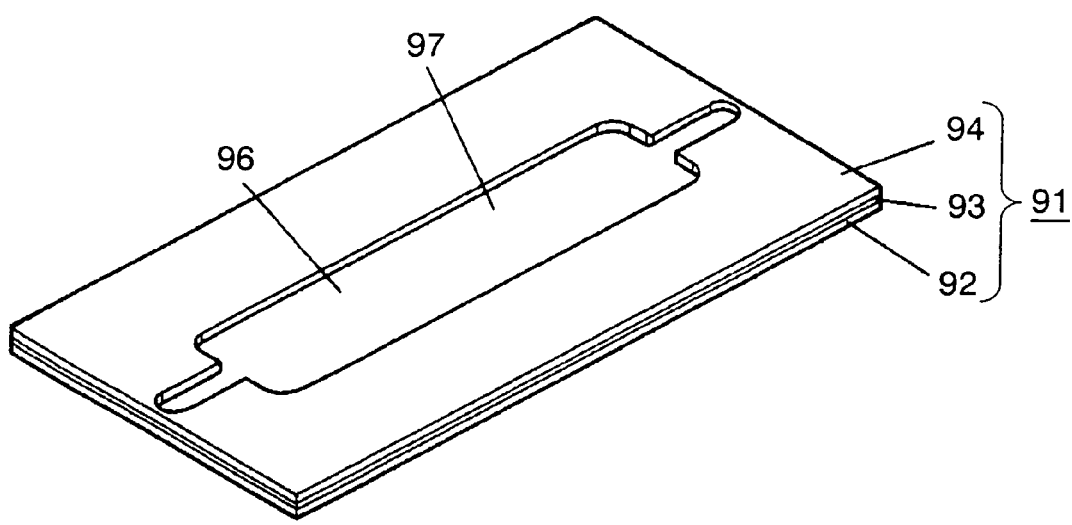
FIG. 28 is a perspective view seen from other side of the substrate shown in FIG. 27.

As is described in the second embodiment, substrates 61, 71, and 81 should preferably be formed of a multi-layered structure made of silicon layers, and silicon dioxide or a glass plate including silicon dioxide. The multi-layered substrate is especially effective in the structure of the embodiment in which flow channels 63, 73, and 83 run beneath the cavity. FIGS. 27 and 28 are perspective views illustrating multi-layered substrate 91 employed for the kit shown in FIG. 16. FIG. 27 shows perspective view of the substrate as seen from the side of cavity 95, while FIG. 28 shows perspective view of the substrate as seen from the side of flow channel 97.

As is apparent from FIGS. 27 and 28, flow channel 97 is separated from cavity 95 by barrier 96 alone that includes silicon dioxide. Such a structure allows cavity 95 and flow channel 97 to have an exact etching depth. Furthermore, as glass plate 93 sandwiched between outer layers separates cavity 95 from flow channel 97, barrier 96 has a consistent thickness.

Compared to silicon, silicon dioxide has lower thermal conductivity. However, the silicon dioxide-containing glass plate 93 can bear the thickness as small as 1 µm. Decreasing the thickness of barrier 96 to at most 10 µm thinner than the silicon barrier can overcome the lower thermal conductivity, which results in achieving high thermal efficiency.

Figure 29:
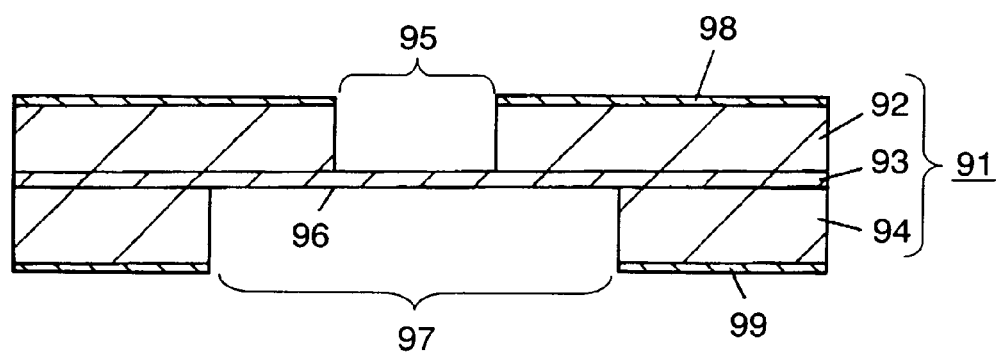
FIGS. 29 and 30 are sectional views illustrating the manufacturing steps of a polymerase chain reaction kit employing the substrate shown in FIG. 27.
Figure 30:
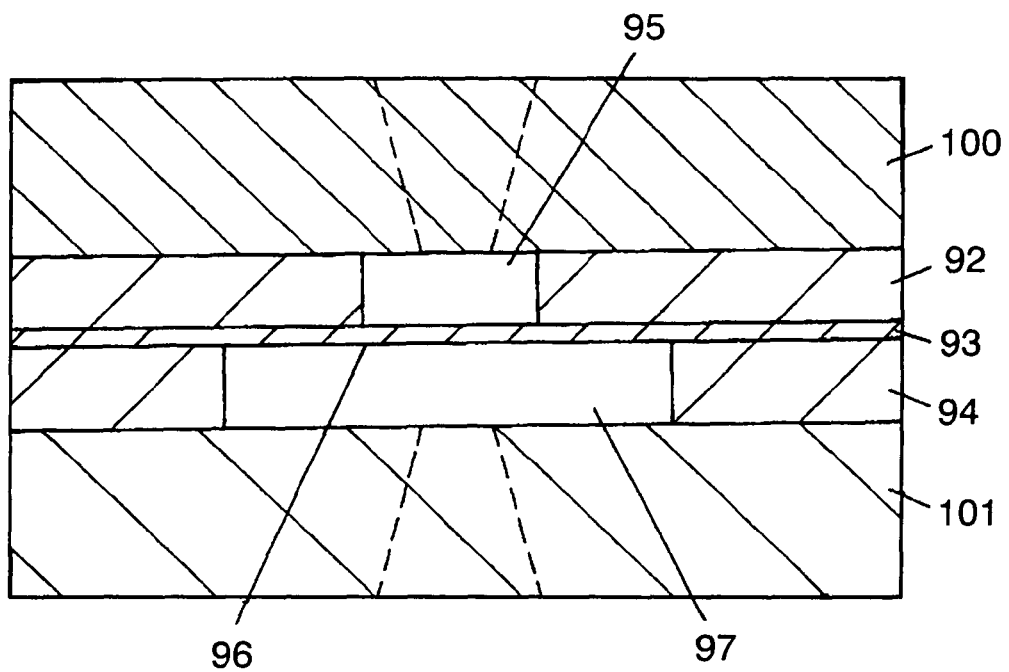

FIGS. 29 and 30 are sectional views illustrating the manufacturing process of the polymerase chain reaction kit having substrate 91. Substrate 91 has, as shown in FIG. 29, a multi-layered structure formed of silicon layers 92 and 94, and glass plate 93 sandwiched therebetween. After the application of resist masks 98 and 99 to the first and the second surfaces, respectively, of substrate 91 by photolithography, the etching for the cavity and the flow channel is performed as is the case described in the first embodiment. The etching rate perceptibly slows down when the etching depth reaches the surface of silicon dioxide-containing glass plate 93. This contributes to the formation of cavity 95 and flow channel 97 with each uniform depth.

Barrier 96, namely glass plate 93 of extremely thin, at most 10 µm, separates cavity 95 and flow channel 97.

Furthermore, attaching first cover plate 100 and second cover plate 101 so as to sandwich substrate 91 completes the polymerase chain reaction kit as shown in FIG. 30.

Fourth Exemplary Embodiment

Figure 31:
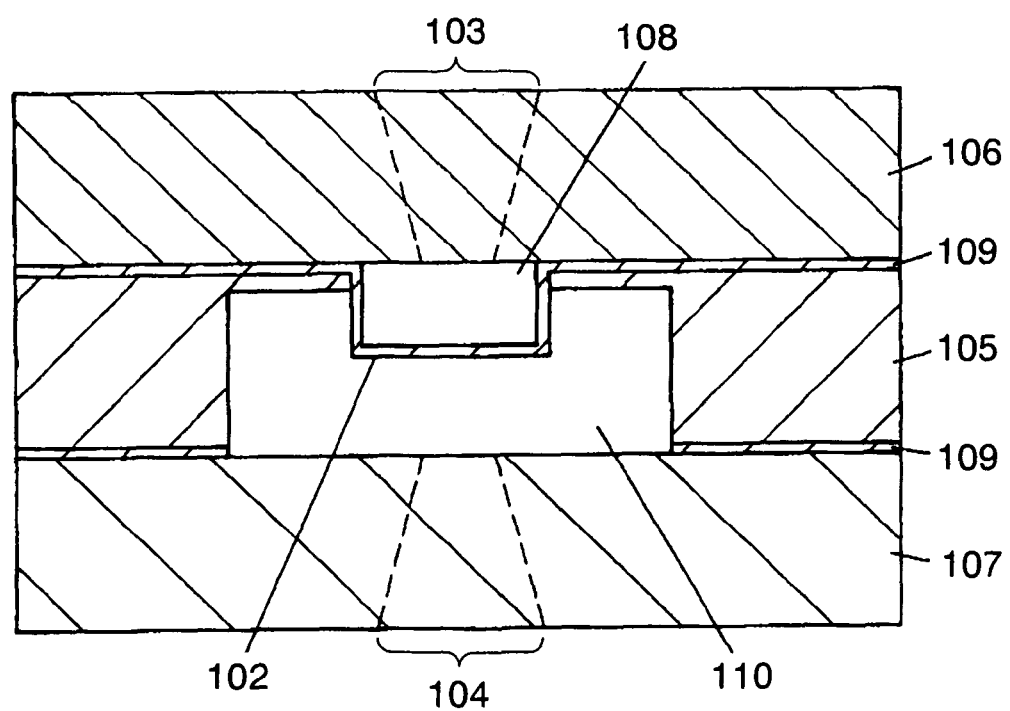
FIG. 31 is a sectional view of a polymerase chain reaction kit of a fourth embodiment.

FIG. 31 is a sectional view illustrating a polymerase chain reaction kit of a fourth embodiment. The inner wall of cavity 108 is, as shown in FIG. 31, formed of silicon dioxide layer 109 alone, and barrier 102 separating the interior of cavity 108 from flow channel 110 is also formed of silicon dioxide layer 109 alone. By virtue of such extremely thin barrier 102, a heating medium running through flow channel 110 can rapidly and uniformly control the temperature of the sample solution contained in cavity 108.

Here will be described the manufacturing process of the polymerase chain reaction kit of the embodiment with reference to the drawings.

Figure 32:
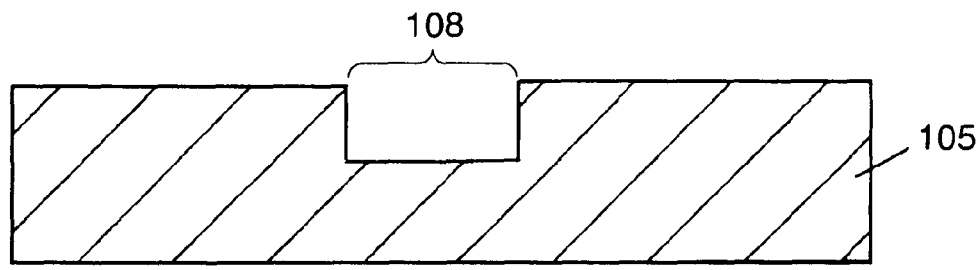
FIGS. 32 through 35 are sectional views illustrating the manufacturing steps of the polymerase chain reaction kit shown in FIG. 31.

FIGS. 32 through 35 are sectional views of the kit in the manufacturing process. Firstly, as shown in FIG. 32, cavity 108 is formed in silicon substrate 105 through dry etching. The etching operation is the same as that described in other embodiments.

Figure 33:
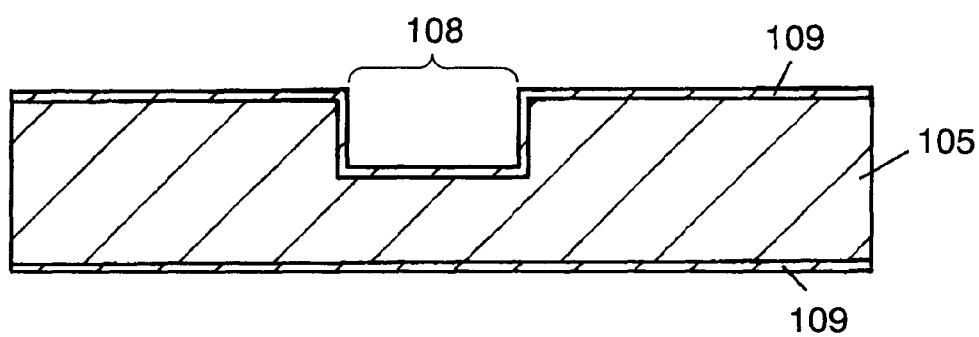

Next, as shown in FIG. 33, silicon dioxide-layer 109 is formed, through thermal oxidation, on all over the surfaces of substrate 105. The applied thickness of silicon dioxide-layer 109 finally becomes the thickness of barrier 102; substrate 105 undergoes the thermal oxidation until barrier 102 obtains a desired thickness. To serve as barrier 102, the applied layer 109 is required to be pinhole-free. Forming the layer at least 2 µm can avoid such fatal defects.

Figure 34:
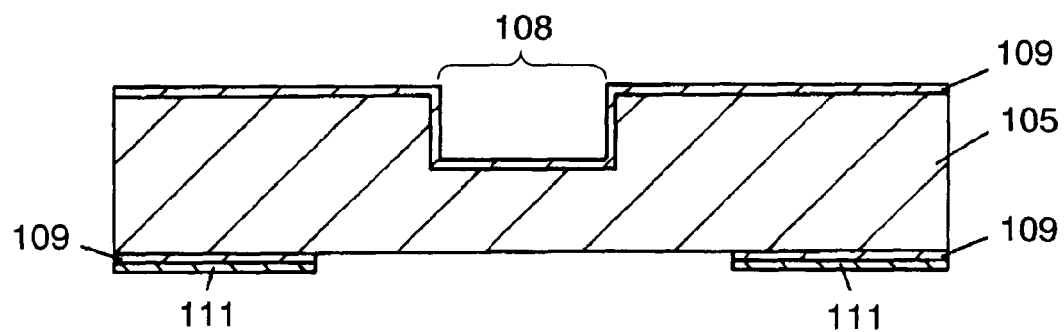

Next, as shown in FIG. 34, resist mask 111 is formed on a second of substrate 105, and then silicon dioxide-layer 109 on substrate 105 is etched. Preferably, resist mask 111 should be applied on substrate 105 so as to have an exposed area greater than the bottom of cavity 108. With the structure, flow channel 110 can be effectively formed along the side sections of cavity 108.

Figure 35:
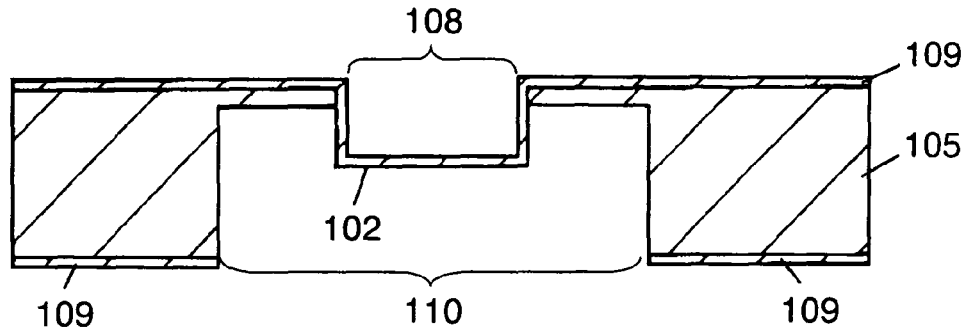

Next, as shown in FIG. 35, substrate 105 is etched at the second surface. The etching increases the depth toward cavity 108 and reaches the bottom of cavity 108 first. The bottom, i.e., barrier 102 is made of silicon dioxide-layer 109. Therefore, barrier 102 is resistant to the etching. Besides, patterning resist mask 111 in which an exposed area is formed greater than the bottom of cavity 108 allows substrate 105 to be etched in the side sections of cavity 108, with the result that cavity 108 formed with silicon dioxide barrier 102 remains.

Leaving a thickness of silicon substrate 105 at the upper section of cavity 108, as shown in FIG. 35, may be effective in reinforcing the structure.

As described earlier, the inner wall of cavity 108 and barrier 102 are made of silicon dioxide layer 109. Furthermore, the thermal oxidation method allows silicon dioxide layer 109 to have a uniform thickness, and also to be extremely thin. With such a structure, a heating medium running through flow channel 110 can control the temperature, with high efficiency, of the sample solution contained in cavity 108.

Other than silicon oxide, barrier 102 of cavity 108 may be formed of silicon nitride, nickel, chrome, gold, and platinum, etc. When these materials are employed, barrier 102 is formed by commonly used thin-film deposition methods. That is, after cavity 108 is formed, the inner wall of barrier 102 undergoes sputtering, vacuum evaporation, chemical vapor deposition (CVD), and plating, instead of the thermal oxidization for the silicon dioxide. In particular, gold and platinum have a thermal conductivity higher than silicon dioxide. Therefore, employing such metals allows the polymerase chain reaction kit to provide more rapid temperature control.

The kit of the embodiment has the structure in which flow channel 110 and cavity 108 are separated by the barrier formed of a material whose etching rate is lower than that of substrate 105. With such a structure, barrier 102 is free from being etched in the etching operation for forming cavity 108 and flow channel 110. Therefore, the cavity, the flow channel, and the barrier can be formed with high precision.

Fifth Exemplary Embodiment

Figure 36:
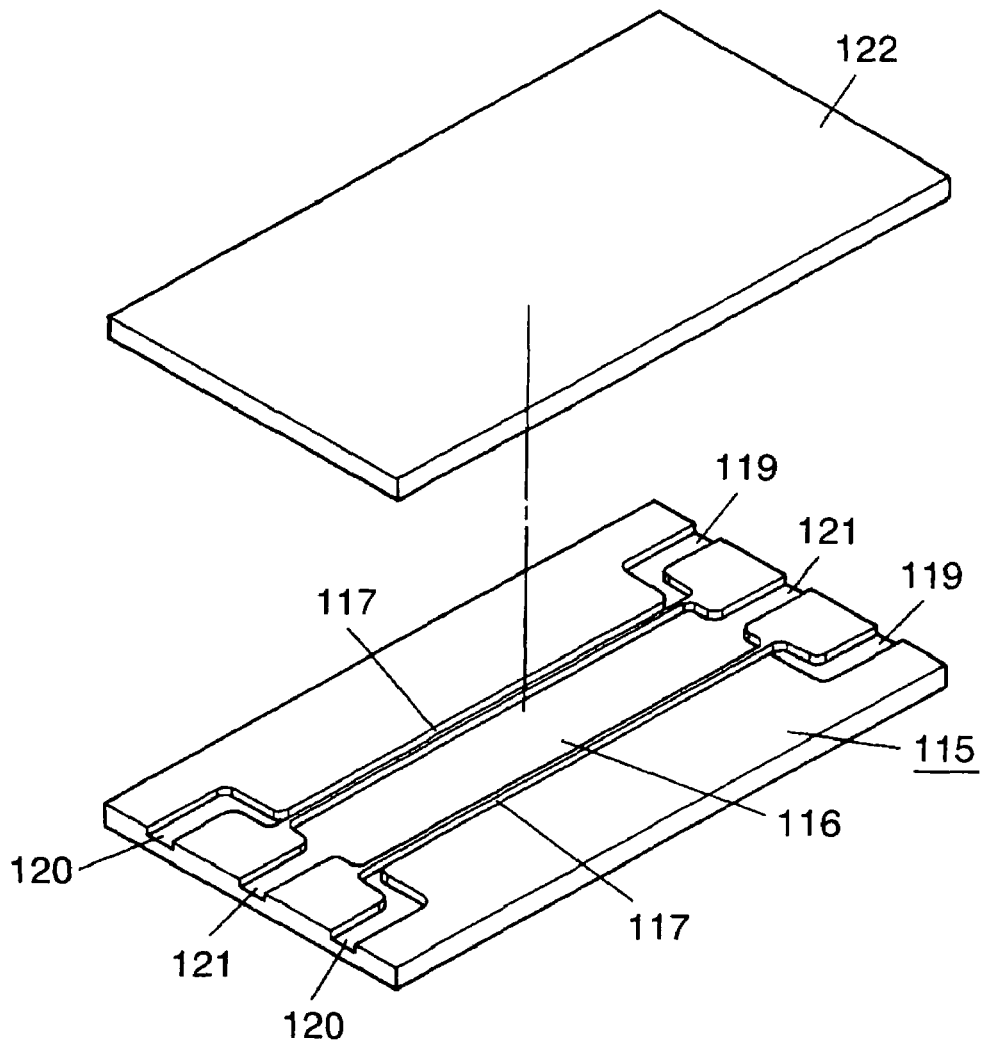
FIG. 36 is an exploded perspective view of a polymerase chain reaction kit of a fifth embodiment.

FIG. 36 is an exploded perspective view of the polymerase chain reaction kit of a fifth embodiment. Like the structure in the first embodiment, substrate 115 has cavity 116 and flow channel 117 on its first surface. The structure differs from the one described in the first embodiment in that sample-injection inlets 121 (hereinafter, inlets 121), flow-in holes 120 and flow-out holes 119 for a heating medium are disposed on both sides of substrate 115. That is, a portion of cavity 116 reaches to the side of substrate 115 and meets inlet 121 there. Similarly, flow channel 117 reaches to the side of substrate 115 and meets flow-in hole 120 and flow-out hole 119. Cavity 116 and flow channel 117 are sealed from the outside by covering the first surface of substrate 115 with cover plate 122. Fluid communication with the outside is provided through inlets 121, flow-in holes 120, and flow-out holes 119. Disposing inlets 121 on both sides of substrate 115—one for injecting a sample solution, and the other for escaping the air from the cavity when the sample solution is injected—facilitates an easy injection. For a kit with a single injection inlet, the injection may be carried out with the help of a centrifugal.

In the aforementioned kit, a sample solution is injected, and a heating medium is set/collected through the holes disposed in the side surfaces of the substrate. That is, there is no need to form these holes in cover plate 122. Such a structure not only allows substrate 115 to have the construction of cavity 116 and flow channel 117 with higher density arrangement, but also allows cover plate 122 to be free from additional processes.

Substrate 115 and cover plate 122 can be formed of materials the same as those of the first embodiment. Silicon substrate 115 paired with glass cover plate 122 is one of the excellent combinations.

Figure 37:
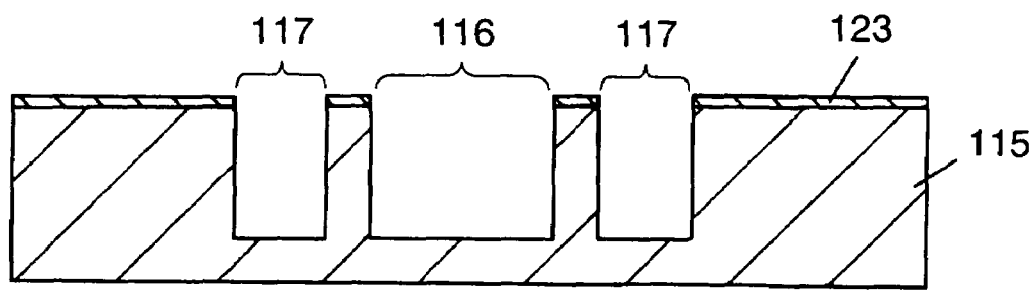
FIGS. 37 through 39 are sectional views illustrating the manufacturing steps of the polymerase chain reaction kit shown in FIG. 36.
Figure 38A:
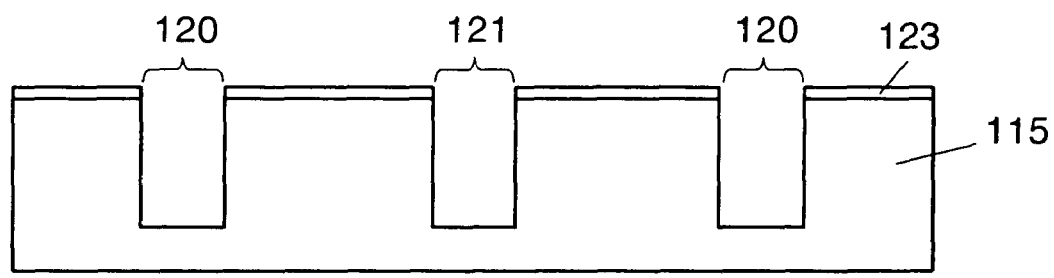
Figure 38B:
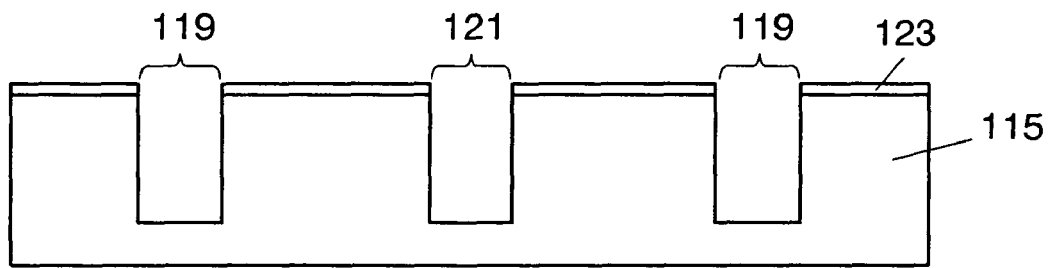
Figure 39:
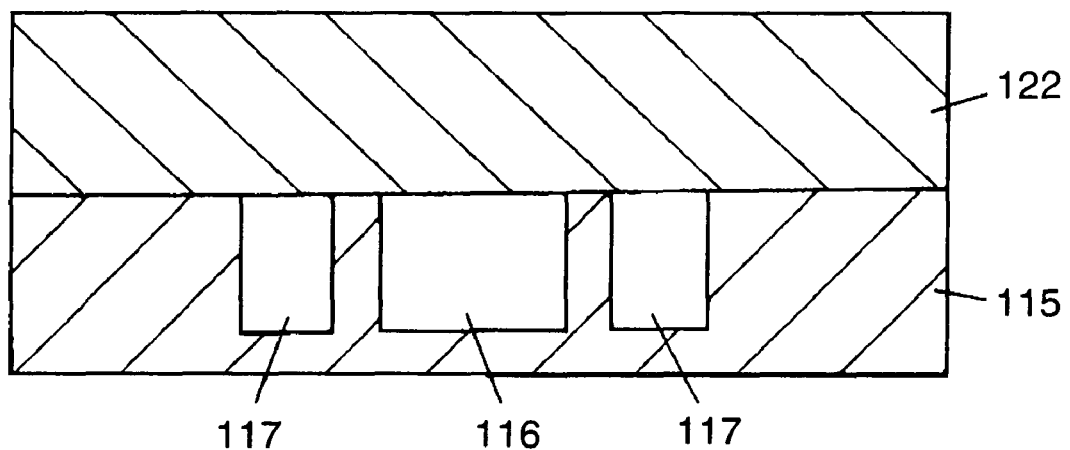

Now will be described the procedure of manufacturing the polymerase chain reaction kit of the embodiment. FIGS. 37 and 39 show sectional views and FIGS. 38A and 38B show side views. The structure of the embodiment differs from the one described in the first embodiment in that substrate 115 is covered with non-processed, i.e., no-hole cover plate 122. As shown in FIG. 37, resist mask 123 is applied on the first surface of substrate 115, and then cavity 116 and flow channel 117 are formed. In the masking process, as shown in FIGS. 38A and 38B, resist mask 123 is applied so that inlet 121, flow-in hole 120, and flow-out hole 119 are formed on the side edge other of substrate 115, and then the etching is performed. After that, cover plate 122 is set on the substrate, as shown in FIG. 39.

Through the processes above, inlet 121, flow-in hole 120 and flow-out hole 119 are formed on the side of substrate 115. To attach glass cover plate 122 with silicon substrate 115, as is the case in the first embodiment, the direct attachment, the anodic attachment, and adhesives are employed.

Although the aforementioned description introduces the process in which inlet 121, flow-in hole 120 and flow-out hole 119 are formed by etching, it is not limited thereto. Inlet 121, flow-in hole 120 and flow-out hole 119 may be formed, for example, by machining, after the formation of cavity 116 and flow channel 117 completes.

Besides, when a plurality of the polymerase chain reaction kits is formed at a time, substrate 115 is bonded to cover plate 122 in the form of a wafer, and then cut off at a predetermined position by dice cutting. The cutting allows individual kits to have flow-in hole 120 and flow-out hole 119 for a heating medium on the sides.

According to the embodiment described above, inlet 121, flow-in hole 120 and flow-out hole 119 are formed on the side of the bonded structure of substrate 115 and cover plate 122. Forming these holes on the side not only allows cover plate 122 to be free from additional processes, but also allows substrate 115 to have the construction of the cavity and the flow channel with higher density arrangement. Forming any one of inlet 121, flow-in hole 120 and flow-out hole 119 on the side can contribute to a high-density construction of the cavity and the flow channel.

It will be understood that the manufacturing method described in the embodiment is applicable with the same advantages to the second, third, and fourth embodiments.

INDUSTRIAL APPLICABILITY

The present invention provides a kit employed for polymerase chain reaction. The kit has a substrate in which a cavity and a flow channel are formed. The flow channel is separated from the cavity by at least a barrier formed along the cavity. Such a structure allows the cavity to be filled with a sample solution even in minute quantities. At the same time, the structure can provide a sample solution with a rapid temperature-control. The structure can therefore contribute to accelerated polymerase chain reaction.

REFERENCE MARKS IN THE DRAWINGS

1: substrate
2: cavity
3: flow channel
4: barrier
5: flow-in groove
6: flow-out groove
7: sample-infection inlet
8: flow-in hole
9: flow-out hole
10: polymerase chain reaction kit
12: cover plate
21: resist mask
22: resist mask
31: attachment plate
32: cover sheet
33: feed-in hole
34: feed-out hole
37: external inlet
38: external outlet
44: substrate
45: cavity
46: flow channel
51: substrate
52: silicon layer
53: glass substrate
54: silicon layer
55: cavity
56: polymerase chain reaction kit
57: flow channel
58: cover plate
59: sample-infection inlet
60: resist mask
61: substrate
62: cavity
63: flow channel
64: first cover plate
65: second cover plate
66: sample-infection inlet
67: flow-out hole
68: polymerase chain reaction kit
69: resist mask
70: resist mask
71: substrate
72: cavity
73: flow channel
74: first cover plate
75: second cover plate
76: sample-infection inlet
77: flow-out hole
78: polymerase chain reaction kit
79: resist mask
80: resist mask
81: substrate
82: cavity
83: flow channel
84: first cover plate
85: second cover plate
86: sample-infection inlet
87: flow-out hole
88: polymerase chain reaction kit
89: resist mask
90: resist mask
91: substrate
92: silicon layer
93: glass substrate
94: silicon layer
95: cavity
96: barrier
97: flow channel 98: resist mask
99: resist mask
100: first cover plate
101: second cover plate
102: barrier
103: sample-infection inlet
104: flow-in hole
105: substrate
106: first cover plate
107: second cover plate
108: cavity
109: silicon dioxide layer
110: flow channel
111: resist mask
115: substrate
116: cavity
117: flow channel
119: flow-out hole
120: flow-in hole
121: sample-infection inlet
122: cover plate
123: resist mask
169: side section (served as a barrier)
179: bottom section (served as a barrier)
189A: bottom section (served as a barrier)
189B: side section (served as a barrier)

c) connecting the cavity to a sample-injection inlet exposed to outside; and
d) connecting the flow channel to a flow-in hole and a flow-out hole exposed to outside.

2. The method of manufacturing a polymerase chain reaction kit of claim 1, wherein the cavity and the flow channel are formed through etching employing at least a promotive gas and a suppressive gas in the a) step.

3. The method of manufacturing a polymerase chain reaction kit of claim 1, wherein the cavity and the flow channel are formed in a same surface of the substrate in the a) step.

4. The method of manufacturing a polymerase chain reaction kit of claim 1, wherein at least any one of the sample-injection inlet, the flow-in hole and the flow-out hole is formed in the cover plate.

5. The method of manufacturing a polymerase chain reaction kit of claim 1, wherein the a) step further includes the sub steps of:
a-1) forming the cavity on a first surface of the substrate; and
a-2) forming the flow channel on a second surface opposite to the first surface of the substrate,
and the plurality of cover plates include a first cover plate for sealing the cavity and a second cover plate for sealing the flow channel.

The invention claimed is:

1. A method of manufacturing a polymerase chain reaction kit comprising the steps of:
a) forming a cavity for holding a sample solution, a barrier, and a flow channel for circulating a heating medium, in a surface of an integral, one-piece substrate, wherein the barrier separates the cavity and the flow channel so that the flow channel is adjacent to a boundary of the cavity defined by the barrier;
b) attaching the substrate to at least one of a plurality of cover plates, thereby sealing at least one of the cavity and the flow channel;

6. The method of manufacturing a polymerase chain reaction kit of claim 5, wherein the sample-injection inlet is formed in the first cover plate, while the flow-in hole and the flow-out hole are formed in the second plate.

7. The method of manufacturing a polymerase chain reaction kit of claim 5 further includes a step of e) forming a layer, which is formed of a material having an etching rate smaller than that of a material forming the substrate, on a inner wall of the cavity.

8. The method of manufacturing a polymerase chain reaction kit of claim 7, wherein the substrate is made of silicon, the layer is made of silicon dioxide, and the layer is formed by any one of i) thermal oxidization, ii) chemical vapor deposition (CVD), and iii) sputtering.

9. The method of manufacturing a polymerase chain reaction kit of claim 7, wherein the substrate is made of silicon, the layer is made of any one of i) gold, ii) platinum, iii) chrome, iv) nickel, and the layer is formed by any one of i) CVD, ii) sputtering, iii) vacuum evaporation, and iv) plating.

10. The method of manufacturing a polymerase chain reaction kit of claim 1, wherein the b) step employs any one of direct attachment and anodic attachment.

11. The method of manufacturing a polymerase chain reaction kit of claim 4, wherein any one of the sample-injection inlet, the flow-in hole and the flow-out hole is formed, by sand blasting, in at least one of the c) step and d) step.

12. The method of manufacturing a polymerase chain reaction kit of claim 1, wherein in the a) step the flow channel is formed to surround the cavity.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gatgagttcg tgtccgtaca act                                              23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggttatcgaa atcagccaca gcgcc                                            25
```